United States Patent
Takle et al.

(10) Patent No.: US 6,558,954 B1
(45) Date of Patent: May 6, 2003

(54) PHENOTYPIC CONVERSION OF CELLS MEDIATED BY EXTERNAL GUIDE SEQUENCES

(75) Inventors: Garry B. Takle, New York, NY (US); Allan R. Goldberg, New York, NY (US); Shaji T. George, New York, NY (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/627,562

(22) Filed: Jul. 28, 2000

Related U.S. Application Data

(63) Continuation of application No. 08/912,378, filed on Aug. 15, 1997, which is a continuation-in-part of application No. PCT/US97/04000, filed on Mar. 14, 1997.
(60) Provisional application No. 60/023,675, filed on Aug. 16, 1996.

(51) Int. Cl.$^7$ .................. C07H 21/04; C12N 15/70; C12N 15/00
(52) U.S. Cl. ................. 435/471; 435/6; 435/91.1; 435/91.31; 435/440; 435/252.1; 536/23.1; 536/24.5
(58) Field of Search ............. 435/6, 69.1, 91.1, 435/91.31, 440, 471, 243, 252.3, 252.31, 252.32, 252.33, 252.34, 252.35, 320.1; 536/23.1, 24.3, 24.32, 24.33, 24.5; 540/145

(56) References Cited

U.S. PATENT DOCUMENTS 5,168,053 A  * 12/1992  Altman et al.

OTHER PUBLICATIONS

Jen et al., Stem Cells, 2000; 18:307–319.*
Green et al., J.A. Coll. Surg., (Jul. 2000), vol. 191, No. 1, pp. 93–105.*
Branch, TIBS (Feb. 1998) 23, pp. 45–50.*
Anderson, W.F., Human Gene Therapy, Nature, vol. 392, SUPP. 30, (Apr. 1998).*
Holm et al., Br. J. Cancer (Aug. 1994), vol. 70, pp. 239–243.*
Kijima et al., Pharmac. Ther. (1995), vol. 68, No. 2, pp. 247–267.*
Barker et al., PNAS (Jan. 1996) vol. 93, pp. 514–518.*

* cited by examiner

*Primary Examiner*—Sean McGarry
(74) *Attorney, Agent, or Firm*—Holland & Knight LLP

(57) ABSTRACT

Disclosed are a method and compositions for delivering nucleic acids to bacterial cells. The method does not require manipulation of the bacteria and is therefore particularly suited to delivery of nucleic acids to bacteria in natural environments, including inside animals bodies. The method generally involves conjugating the nucleic acid to be delivered with a cationic porphyrin and bringing the conjugate and the target bacterial cells into contact. Both the porphyrin and conjugated nucleic acid are taken up by the bacterial cells and the nucleic acid can then have a biological effect on the cells. Specifically disclosed is a method for converting drug-resistant bacterial cells to drug-sensitive cells by delivery of external guide sequences to the cells which then promote cleavage of RNA molecules involved in conferring the drug-resistant phenotype on the cells. The drug-resistant phenotype of the cells is thus converted to a drug-sensitive phenotype. The drug-sensitive cells are then susceptible to drug therapy. Also disclosed is a method and compositions for killing eukaryotic pathogens or converting drug-resistant eukaryotic cells to drug-sensitive cells. The method involves the delivery of external guide sequences, ribozymes, or vectors encoding external guide sequences or ribozymes, to eukaryotic cells. Preferred target eukaryotic cells for the disclosed method include algae, protozoa, fungi, slime mold, and cells of helminths.

8 Claims, 5 Drawing Sheets

PHENOTYPIC CONVERSION OF CELLS MEDIATED BY EXTERNAL GUIDE SEQUENCES

CROSS-REFERENCE TO RELATED APPLICATIONS

This application is a continuation of copending application Ser. No. 08/912,378, filed Aug. 15, 1997, and a continuation-in-part of International Application PCT/US97/04000 filed Mar. 14, 1997. This application claims benefit of U.S. Provisional Application No. 60/023,675, filed Aug. 16, 1996. Application Ser. No. 09/912,378, filed Aug. 15, 1997, and U.S. Provisional Application No. 60/023,675, filed Aug. 16, 1996, are hereby incorporated herein by reference.

BACKGROUND OF THE INVENTION

The present invention is generally in the fields of delivery of nucleic acids to bacteria and of using external guide sequences to convert the phenotype of pathogens.

Many techniques have been developed for getting nucleic acids into bacterial cells. Early techniques made use of naturally occurring systems of genetic transfer, including bacteriophage and bacterial conjugation (Goodenough, "Genetics", 2nd ed. (Holt Rinehart Winston, New York, 1978), pages 397–436). Bacteriophage can transfer not only viral nucleic acid, but occasionally also transfer bacterial nucleic acid accidently encapsidated in the phage (a process referred to as transduction). In bacterial conjugation, Hfr (high frequency of recombination) cells contained genes that mediated an orderly, linear transfer of a bacterial chromosome or other genetic element from one bacterial cell to another. Both systems were generally limited to the transfer of nucleic acid already present in a bacterial cell. With the advent of recombinant DNA technology, both the need and means for getting nucleic acids into bacterial cells increased. In vitro manipulation and adaptation of natural episomal plasmids and bacteriophage allowed the formation of novel nucleic acids and the cloning of genes. However, effective use of recombinant technology was limited to those cells for which methods of introduction of nucleic acids had been developed.

Although some cells will spontaneously take up some nucleic acids, efficient uptake required the development of methods to increase the permeability and/or for physical manipulation of cells. Examples of these techniques include transformation (via increased permeability), transfection (transformation of viral vectors), electroporation (electrically stimulated uptake), and microinjection (physical injection of nucleic acids). For example, efficient uptake of nucleic acids by the popular laboratory bacterium *Escherichia coli* requires salt treatments to increase the permeability of the cell wall and membrane followed by a heat shock to cause the cell to actually internalize adhered nucleic acid. Electroporation is commonly used for eukaryotic cells and uses an electric shock to cause internalization of nucleic acids. For cells with a cell wall (such as yeast, most plant cells, and many bacteria), uptake of nucleic acids generally requires that the cell wall be enzymatically digested. Nearly all methods of getting nucleic acids into bacterial cells requires treatment or manipulation of the cells. Such manipulations are difficult or impossible to use on bacterial cells in their natural environment, especially for those bacteria colonizing or infected plants and animals.

Drug resistance in pathogens are a problem of clinical importance. The use, and misuse, of antibiotics and other drugs meant to control the growth of pathogens has led to an increasing number of organisms having resistance to the effects of the drugs. The standard approach to this problem has consisted of attempts to discover new drugs to which the organisms are sensitive, an expensive and time-consuming process. To further complicate matters, organisms continue to mutate to acquire resistance to newly developed drugs.

It is therefore an object of the present invention to provide a method and compositions for delivering nucleic acids to bacterial cells.

It is also an object of the present invention to provide a method for converting drug-resistant bacterial cells to drug-sensitive bacterial cells.

It is also an object of the present invention to provide a means for killing or reducing the viability of eukaryotic pathogens.

It is also an object of the present invention to provide a means for converting drug-resistant eukaryotic cells to drug-sensitive eukaryotic cells.

SUMMARY OF THE INVENTION

Disclosed are a method and compositions for delivering nucleic acids to bacterial cells. The method does not require manipulation of the bacteria and is therefore particularly suited to delivery of nucleic acids to bacteria in natural environments, including to bacteria inside animals bodies. The method generally involves conjugating the nucleic acid to be delivered with a cationic porphyrin and bringing the conjugate and the target bacterial cells into contact. Both the porphyrin and conjugated nucleic acid are taken up by the bacterial cells and the nucleic acid can then have a biological effect on the cells. Preferred nucleic acids for delivery using the disclosed method include external guide sequences, ribozymes, plasmids and other vectors, and antisense nucleic acids.

Specifically disclosed is a method for converting drug-resistant bacterial cells to drug-sensitive cells by delivery of external guide sequences to the cells which then promote cleavage of RNA molecules involved in conferring the drug-resistant phenotype on the cells. The drug-resistant phenotype of the cells is thus converted to a drug-sensitive phenotype. The drug-sensitive cells are then susceptible to drug therapy. Also disclosed is a method and compositions for killing or reducing the viability of eukaryotic pathogens, or converting drug-resistant eukaryotic cells to drug-sensitive cells. The method involves the delivery of external guide sequences, ribozymes, or vectors encoding external guide sequences or ribozymes, to the eukaryotic cells. Preferred target eukaryotic cells for the disclosed method include algae, protozoa, fungi, slime mold, and cells of helminths.

The use, and misuse, of antibiotics and other drugs meant to control the growth of pathogens has led to an increasing number of organisms having resistance to the effects of the drugs. Such resistance often results from the acquisition of a gene or genes conferring resistance on the organism, or an increase in the prevalence of certain alleles, which confer resistance on the organism, through selective pressure. The disclosed method and compositions can be used to attack such genetically based drug resistance.

Porphyrins or phthalocyanins (referred to jointly herein as "porphyrins" unless otherwise stated) or other macrocyclic compounds are useful in the disclosed method and compositions. The system is extremely simple, since the two principle components are a porphyrin having a net overall positive charge, as defined in more detail below, and the nucleic acid to be delivered, which has a net overall negative charge. The porphyrin binds the compound to be delivered and enhances uptake of the nucleic acid. The porphyrin also enhances the stability of the complexed nucleic acid against nuclease disgestion.

As demonstrated by the examples, in a preferred embodiment the nucleic acid is an oligonucleotide which binds to the porphyrin in a stoichiometric ratio, and greatly enhances uptake by cells. The examples demonstrate delivery to a variety of bacteria. The disclosed method and compositions have utility in delivery of nucleic acids to bacterial cells, both in culture and in natural environments such as in plants and animals (including humans). Delivery of nucleic acids to bacteria has many known utilities, including genetic manipulation of bacteria and for diagnostic purposes, and the disclosed method can be used to effect any of these known purposes. Delivery of nucleic acids to bacteria infecting animals and humans can be used for therapeutic effect, for example, by altering, weakening, or killing the bacteria to which the nucleic acid is delivered.

Ribozymes can be used to cleave genetic elements which are required for cell viability or which confer drug resistance on eukaryotic pathogens. In a preferred embodiment, the ribozyme is RNAase P, which is directed to cleave the genetic element by external guide sequences ("EGS") targeted to the element. EGSs (Forster and Altman, *Science* 249:783–786 (1990); Yuan et al., *Proc. Natl. Acad. Sci. USA* 89:8006–8010 (1992)) directing RNAase P to cleave are oligonucleotides that, in combination with an RNA molecule to be cleaved, form a structure recognized by RNAse P as a substrate. Preferred prokaryotic EGSs have nucleotides complementary to the nucleotides 3' to the cleavage site in the RNA to be cleaved and at its 5' terminus the nucleotides NCCA, where N is any nucleotide. Preferred eukaryotic EGSs have nucleotides complementary to the RNA to be cleaved such that the EGS and RNA to be cleaved together form structures similar to at least the aminoacyl and T stems of tRNA. In other embodiments, ribozymes are administered to cleave the genetic elements. A preferred form of the disclosed method involves delivery of eukaryotic EGS to a pathogenic eukaryotic cell, either as an EGS molecule or encoded by a vector for production of the EGS in the pathogen, where the EGS promotes cleavage by endogenous RNAase P of RNA transcribed from a targeted gene. The eukaryotic cells to be targeted in the disclosed method can be in vitro or in or on plants, animals, or humans.

DETAILED DESCRIPTION OF THE INVENTION

Figure 1A:
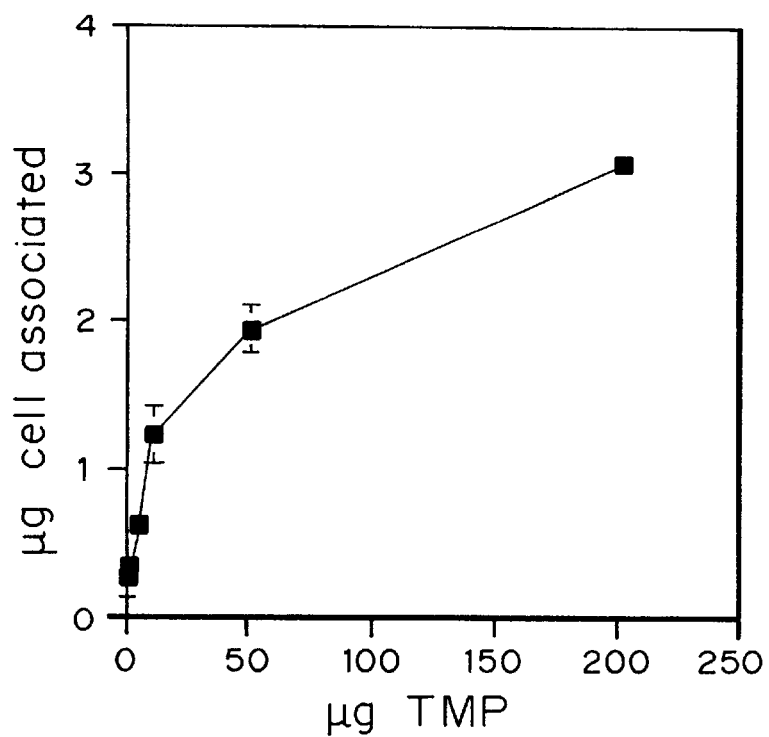
FIG. 1A is a graph of the number of micrograms of cell-associated EGS as a function of the number of micrograms of porphyrin originally complexed with the EGS.

A method of, and compositions for, delivering nucleic acids to bacterial cells has been developed. The compositions are complexes and conjugates of cationic porphyrin and the nucleic acid to be delivered. The conjugate is formed by ionic interaction of the negatively charged nucleic acid and the positively charged porphyrin. The method involves bringing into contact the target bacterial cells and the porphyrin/nucleic acid conjugates.

It has been determined that cationic porphyrins are able to deliver high concentrations of oligonucleotides to tissue culture cells of various types (hepatocytes, promyelocytes, kidney epithelial cells). The examples below describe the delivery of external guide sequences (EGS), oligoribonucleotides that direct cleavage at specific sites on target RNAs by RNAase P, to bacteria. The data demonstrate that cationic porphyrins are able to mediate delivery of EGSs into bacterial cells to a level that will allow these oligoribonucleotides to effectively mediate cleavage of a target RNA. For this use, the target RNA can be chosen to alter or eliminate the effect of the RNA such that the phenotype of the cell is altered in a useful way. For example, by targeting a critical RNA, a bacterial cell can be killed or weakened. By targeting an RNA involved in conferring some characteristic or property on the cell, the characteristic can be altered or eliminated. Such an alteration could then be exploited for some other purpose. A preferred target of the EGS delivered using the disclosed method is RNA involved in conferring drug resistance on the bacterial cell. This allows the conversion of a drug-resistant bacterial cell to a drug-sensitive bacterial cell.

Also disclosed is a method of killing or reducing the viability of a eukaryotic pathogen or converting the phenotype of a drug-resistant eukaryotic cell to a drug-sensitive phenotype. The method involves cleavage of an RNA molecule required for cell viability or involved in conferring drug resistance on a eukaryotic cell (or on an organism containing the cell). The RNA is cleaved by a ribozyme which is targeted to the RNA molecule required for cell viability or involved in conferring drug resistance. Targeting of, and cleavage by, the ribozyme can be accomplished in several ways. In one embodiment, a ribozyme is designed to target the RNA molecule by selection of an appropriate guide sequence. Examples of targetable ribozymes include hammerhead ribozymes, axehead ribozymes, group I intron ribozymes, and the catalytic subunit of RNAase P coupled to a guide sequence. The ribozyme targeted to the RNA molecule can then be made to cleave the target RNA molecule by delivering the ribozyme to the eukaryotic cell or by delivering a vector encoding the ribozyme to the eukaryotic cell. In the latter case the vector is designed to express the ribozyme in the cell. In this way the ribozyme is brought into contact with the target RNA molecule, the RNA molecule is cleaved, and the eukaryotic cell (or organism containing the cell) is killed or rendered drug sensitive.

In another embodiment, an external guide sequence (EGS) is designed to promote cleavage of the targeted RNA molecule by RNAase P present in the eukaryotic cell. The EGS targeted to the RNA molecule can then be made to promote cleavage of the target RNA molecule by delivering the EGS to the eukaryotic cell or by delivering a vector encoding the EGS to the eukaryotic cell. In the latter case the vector is designed to express the EGS in the cell. In this way the EGS is brought into contact with the target RNA molecule, the EGS and target RNA form a complex recognized by RNAase P as a substrate, the RNA molecule is cleaved by RNAase P, and the eukaryotic cell (or organism containing the cell) is killed or rendered drug sensitive.

I. MATERIALS

The disclosed compositions for delivery of nucleic acids to prokaryotic cells are a combination of a macrocyclic compound and the nucleic acid. In the preferred embodiments, the macrocyclic compounds are porphyrins or phthalocyanins; in the most preferred embodiment, the porphyrins are water soluble. The nucleic acid to be delivered has a net overall negative charge; the macrocyclic compound has a net overall positive charge under physiological conditions (that is, a pH of approximately 7.0 to 7.5, more typically 7.2 to 7.4). As a result, the nucleic acid to be delivered is ionically bound to the macrocyclic compound until it and the bound nucleic acids are internalized in the targeted cells.

It has been discovered that nucleic acid compositions including porphyrins enhance the uptake of the nucleic acid by bacterial cells. Thus, compositions including porphyrins are a preferred form of composition for delivering nucleic acids to bacterial cells.

For phenotypic conversion of drug-resistant cells, disclosed are external guide sequences directed against RNA molecules involved in conferring drug resistance. Ribozymes directed against RNA molecules involved in conferring drug resistance on a eukaryotic cell, and DNA encoding ribozymes and EGS molecules directed against RNA molecules involved in conferring drug resistance on a eukaryotic cell, are also disclosed for phenotypic conversion of drug-resistant eukaryotic cells.

A. Porphyrins, Phthalocyanins and other Macrocycles

The photochemistry and photophysics of porphyrins, metalloporphyrins, and phthalocyanines have been studied in detail. Processes observed include loss of an axial ligand, energy transfer, electron transfer, formation of singlet oxygen, phosphorescence and fluorescence. The photoprocesses observed in each system depend greatly on the central ligand, normally a metal (2H for porphyrin), the oxidation state of the metal and the axial ligand bound to the metal. A weaker dependence of the photophysical properties on the nature of the macrocycle is observed. Porphyrins and phthalocyanines have been reported to have a variety of other biological activities, including some anti-HIV activity. However, relatively little has been done with them with respect to in vivo clinical applications other than in photodynamic tumor therapy.

Porphyrins are macrocycle compounds with bridges of one carbon atom or one nitrogen atom respectively, joining the pyrroles to form the characteristic tetrapyrrole ring structure. There are many different classes of porphyrin-like compounds. The term porphyrins will be used herein to refer to porphyrins, phthalocyanines, chlorins, metallo derivatives thereof, and other porphyrin-like compounds or macrocycles possessing antiviral activity or which are positively charged and therefore capable of binding to oligonucleotides and other negatively charged compounds to be delivered.

Those porphyrins and phthalocyanins that are useful in the methods and compositions described herein for delivery of compounds have an overall net negative charge; are water soluble, defined herein as soluble to at least a level of 20 mg/ml saline, and have a net overall positive charge, for example, compounds containing a quaternary methyl amine groups synthesized by interaction of a tertiary amine with a nucleophile.

Some porphyrins are isolated from nature, for example, protoporphyrin IX, which is the organic portion of hemin. Many derivatives of natural porphyrins are known (see, for example, Smith and Cavaleiro, "Protoporphyrin-IX: Some Useful Substituent Manipulations", *Heterocycles*, 26:1947–1963, (1986)). Many other porphyrins and phthalocyanines are synthesized in the laboratory. These include those made via the condensation of aldehydes and pyrroles, such as tetraphenylporphyrin. They also include compounds built up from smaller organic fragments.

Porphyrin-like compounds can have one or more substituents, and combinations of one or more different substituents. The substituents can be symmetrically or asymmetrically located. The substituents, as well as the overall structure, can be neutral, positively charged or negatively charged. Charged structures have counterions, and many counterions and combinations of counterions are possible.

Porphyrins can be covalently attached to other molecules, for example, cyclodextrins (Gonzalez and Weedon, *Can. J. Chem.* 63:602–608 (1985)). They can have an attached molecular superstructure. The conjugation of the ring can be altered by addition of one or more substituents. In addition, metals can be inserted into the tetrapyrrole ring. Examples of such metals include, but are not limited to, Fe, Co, Zn, Mo, Ti, Mn, Cr, Ni, Mg, Cu, Tl, In, Ru, V and Au. Additional ligands can be attached to the metal.

Both natural and synthetic porphyrins, phthalocyanines and metallo derivatives can be used. Examples include 5,10-Diphenyl-15,20-di(N-methyl-3-pyridyl)-porphyrin; 5,10-Diphenyl-15,20-di(N-methyl-4-pyridyl)-porphyrin; 5,15-Diphenyl-10,20-di(N-methyl-3-pyridyl)-porphyrin; Hemin; Protoporphyrin; meso-tetra-(N-methyl-4-pyridyl)-porphyrin; Meso-tetraphenylporphine; Protoporphyrin IX dimethyl ester; meso-tetra-(4-carboxyphenyl)-porphyrin; meso-tetra-(4-methylphenyl)-porphyrin; meso-tetra-(3-methylphenyl)-porphyrin; meso-tetra-(4-hydroxyphenyl)-porphyrin; Fe(III)-tetraphenyl-porphyrin; meso-tetra-(4-chlorophenyl)-porphyrin; Fe(III)-tetra-(4-methylphenyl)-porphyrin; Fe(III)-tetra-(N-methyl-4-pyridyl)-porphyrin; Fe(III)-mu-oxo-dimer of tetraphenylporphyrin; nickel phthalocyanine tetrasulfonic acid; copper phthalocyanine 3,4',4'',4'''-tetrasulfonic acid; and copper phthalocyanine.

Examples of synthetic porphyrins include 5,10-Diphenyl-15,20-di(N-methyl-3-pyridyl)-porphyrin Cl-, 5,10-Diphenyl-15,20-di(N-methyl-4-pyridyl)-porphyrin Cl-, 5-Diphenyl-10,20-di(N-methyl-4-pyridyl)-Cl-porphyrin Cl-, 5,15-Diphenyl-10,20-di(N-methyl-3-pyridyl)-porphyrin Cl-, meso-tetra-(N-methyl-4-pyridyl), porphyrin tosylate salt (TMP), meso-tetraphenylporphine (TPP), meso-tetra-(4-carboxyphenyl)-porphyrin (TPP(4-CO$_2$H)$_4$), meso-tetra-(4-methylphenyl), porphyrin (TPP(4-Me)$_4$), meso-tetra-(3-methylphenyl)-porphyrin (TPP(3-Me)$_4$), meso-tetra-(4-hydroxyphenyl)-porphyrin (TPP(4-OH)$_4$), meso-tetra-(4-chlorophenyl)-porphyrin (TPP(4-Cl)$_4$), and meso-tetra-(4-N,N,N, trimethylanilinium)porphyrin.

Examples of synthetic metalloporphyrins include Fe(III)-tetraphenylporphyrin chloride (FeTPPCl), Fe(III)-tetra-(4- methylphenyl)-porphyrin chloride (FeTPP)(4-Cl)$_4$, Fe(III)-tetra-(N-methyl-4-pyridyl)-porphyrin chloride (FeTMPyP), Fe(III)-mu-oxo-dimer of tetraphenyl-porphyrin ($\mu$-oxo-TPP), Cu(II)-5,10-diphenyl-15,20-di(N-methyl-4-pyridyl)-porphyrin (Cu-CP4), Ni(II)-5,10-diphenyl-15,20-di(N-methyl-4-pyridyl)-porphyrin (Ni-CP4), and Fe(III)-meso-tetra-(4-N,N,N, trimethylanilinium)porphyrin.

Examples of phthalocyanines include Copper phthalocyanine tetrasulfonic acid tetra-sodium salt (CuPHTHS$_4$), Nickel phthalocyanine tetrasulfonic acid (NiPHTHS$_4$), Copper phthalocyanine 3,4', 4",4'"-tetrasulfonic acid (CuPHTHS$_4$)(3,4,4,4), Copper phthalocyanine (CuPHTH), Copper-4,4',4",4'"-tetra-aza-29H.

Protohemin can be obtained from Aldrich Chemical Co., Milwaukee, Wis. Fe(III) tetraphenylporphyrin derivatives were either purchased from Midcentury Chemicals or synthesized by pyrrole-benzaldehyde condensation in a propionic acid reflux, by the method of Adler et al., *J. Org. Chem.*, 32:476 (1967). Iron can be inserted using FeCl$_2$ in dimethylformamide, as taught by Adler et al., *Inorg. Syn.*, 16:213–220 (1976). General synthetic references are Dolphin, Ed., "The Porphyrins", Vol. 6, Chap 3–10, pages 290–339 (Academic Press: New York, 1979); Morgan and Dolphin, *Struct. Bonding* (Berlin), 64 (Met. Complexes Tetrapyrrole Ligands I), pages 115–203 (1987); Smith et al., *Heterocycles*, 26(7):1947–63 (1987).

Still other synthetic techniques include the methods of Lindsey et al., *J. Org. Chem.* 52:827–836 (1987); Momenteau et al., *J. Chem. Soc., Perkin Trans. I.* 283 (1988); Morgan and Dolphin, *J. Org. Chem.* 52:5364–5374 (1987); Smith et al., *J. Org. Chem.* 51:666–671 (1986); and Smith and Minnetian, *J. Chem. Soc., Perkin Trans.* I. 277–280 (1986). Other references to metal insertion include Buchler, "The Porphyrins", vol. 1, ch. 10, Dolphin, ed. (Academic Press, NY 1979); Lavallee, *Coord. Chem. Rev.* 61:55–96 (1985); Lavallee, *Comments Inorg. Chem.* 5:155–174 (1986).

Phthalocyanines can be synthesized by the condensation of phthalonitrile and its derivatives. Functionalization of the phthalocyanine ring system is readily achieved, using the method of Langlois et al., "Biological activities of phthalocyanines—IV. Type II sensitized photoxidation of L-tryptophan and cholesterol by sulfonated metallo phthalocyanines." *Photochem. Photobiol.*, 44:117–123 (1986), and Spikes, *Photochem. Photobiol.*, 43:691–699, (1986).

Porphyrins and phthalocyanines may also be obtained from commercial sources including Aldrich Chemical Co., Milwaukee, Wis., Porphyrin Products, Logan, Utah, and Midcentury Chemicals, Posen, Ill.

Chlorins, another group of useful porphyrins, can be made using the method described by Oseroff et al., *Proc. Natl. Acad. Sci. USA*, 83, 8744–8748 (1986).

Examples of natural porphyrins are Protoporphyrin, disodium salt (PPIX) and Protoporphyrin IX dimethyl ester (PPIXDME). Examples of natural metalloporphyrins include hemin, bovine, (chloroprotoporphyrin IX Fe(III)) (FePPIXCl).

Metalloporphyrins are organic compounds whose structure includes a porphyrin ring which contains in its center a prosthetic metal atom, such as iron or magnesium, held by four inwardly-facing nitrogen atoms. Metalloporphyrins have been found associated with a variety of proteins such as globin, myoglobin and cytochromes, and in pigment molecules, such as chlorophylls. Such proteins consist of the metalloporphyrin moiety and the remaining portion comprising the protein called the apoprotein.

Heme, the common metalloporphyrin found in hemoglobin and cytochromes, is synthesized in animal cells by the chelation of an atom of iron with protoporphyrin IX using ferrochelatase. In hemoglobin, the heme molecule confers a reversible oxygen-binding capacity, whereas in cytochromes heme functions in electron transfer. Heme is a planar molecule and is capable of intercalating into double-stranded DNA (Aft and Mueller, *J. Biol. Chem.* 258:12069–12072 (1983); Carvlin et al., *Nucleic Acids Res.* 11:6121–6139 (1983)) and within lipid bilayers (Cannon et al., *Biochem.* 23:3715–3721 (1984); Tipping et al., *Biochem. J.* 180:327–337 (1979)). Heme contains two carboxyl groups which can serve as sites for peptide bond formation with amino group-containing molecules. Heme is readily available as an inexpensive reagent in the form of heme chloride (hemin, Sigma Chemical Co., St. Louis, Mo.).

A heme derivative that can be used instead of heme is an aminodiglyceride such as dioleoylphosphatidyl ethanolamine which contains a heme molecule attached to the ethanolamine residue, or other diglyceride with a heme group attached directly to the glycerol. These lipids can be included directly during the formation of liposomes.

The interaction of water soluble porphyrins with nucleic acids has been looked at by several workers as a method for investigating the higher structures of DNA and for helping to understand porphyrin drug:nucleic acid associations (Villenueva and Jori, "Pharmokinetic and tumor-photosensitizing properties of the porphyrin meso-tetra (4N-methylpyridyl)porphine" *Cancer Lett.* 73:59–64 (1993); Gibbs et al., "Interactions of porphyrins with purified DNA and more highly organized structures" *J. Inorg. Biochem.* 32:39–65 (1988); Gibbs et al., "Self-assembly of porphyrins on nucleic acid templates" *Biochem. Biophys. Res. Comm.* 157:350–358 (1988); Gibbs and Pasternack, "Interactions of porphyrins and metalloporphyrins with nucleic acids" *Seminars in Hematology*, 26:77–85 (1989); Pasternack et al., "The influence of ionic strength on the binding of a water-soluble porphyrin to nucleic acids" *Nucl. Acids Res.* 14:5919–5931 (1986); Carvlin and Fiel, "Intercalative and non-intercalative binding of large cationic porphyrin ligands to calf thymus DNA" *Nucl. Acids Res.* 11:6121–6139 (1983)). Water soluble porphyrins have been shown to be capable of crossing the nuclear membrane (Gibbs et al. (1988)) and have well-documented effects on naked DNA and chromatin during phototherapy (Aft and Mueller, "Hemin-mediated DNA strand scission" *J. Biol. Chem.* 258:12069–12072 (1983)). Porphyrins are well known to be tumor localizers and for this reason these water soluble cationic versions have attracted attention. Water soluble anionic porphyrins have been conjugated to oligonucleotides as a method for the site-specific cleavage of the target sequence photoinduced by the porphyrin after hybridization (Ortigao et al., "Solid-phase introduction and intracellular photoinduced reaction of a water-soluble meso-tetracarboxyporphine conjugated to an antisense oligodeoxyribonucleotide" *Biochimie* 75:29–34 (1993)). The porphyrin described in the latter work localizes however to the cytoplasm, and exerts its effect only after laser light has been passed through cells.

Methods for Coupling of Macrocycles to Nucleic Acids

As discussed above, the nucleic acids to be delivered can be coupled to the porphyrin or other macrocycle ionically. The nucleic acids can also be coupled covalently.

Methods for covalently crosslinking porphyrins to nucleic acids are known. For example, a heme molecule has two pendant carboxyl groups, two pendant alkene groups and four methyl groups. The carboxyl groups can be used to ionically or covalently link a nucleic acid to the heme molecule. The carboxyl groups in a heme molecule can react in an acid-base reaction with amine groups on a nucleic acid to form an ionic bond. The carboxyl groups can also be reacted with hydroxy groups on a nucleic acid using a multi-valent ion, such as $Ca^{++}$ to effect the coupling. The carboxyl groups in a heme molecule can be reacted with pendant hydroxy, amine, thiol or carboxy groups on a nucleic acid by means known to those skilled in the art of organic synthesis, for example, using a dehydrating agent such as DCC. The resulting products are esters, amides, thioesters and anhydrides, respectively. Representative methods are listed in Larock, "Comprehensive Organic Transformation", VCH, New York, 966–972 (1989). The alkene and methyl groups can form radicals, which can be used to covalently link a nucleic acid to the heme molecule. To link the nucleic acid to the heme molecule, the polymer needs to have at least one reactive group that reacts with a carboxyl group, an alkene group or a methyl radical to form an ionic or covalent bond. The pendant alkene groups in a heme molecule can be covalently coupled to a nucleic acid containing alkene groups using a free-radical initiator. To crosslink the nucleic acid and the heme molecule, the nucleic acid must have at least two reactive groups.

The pendant methyl groups form radicals when subjected to UV or gamma radiation. The methyl groups can be coupled to nucleic acids containing pendant aliphatic carbon-hydrogen, carbon-chlorine or carbon-bromine bonds by subjecting the methyl groups on the heme molecule to UV or gamma radiation in the presence of the nucleic acid.

B. Nucleic Acids

Any nucleic acid or nucleic acid derivative can be used in the disclosed porphyrin compositions and delivered to bacterial cells using the disclosed method. As used herein, the terms nucleic acid and nucleic acid molecule include any nucleic acid molecules, especially ribozymes, external guide sequences, vectors, aptamers, triplex molecules and antisense oligonucleotides. Preferred nucleic acids are ribozymes, external guide sequences, and antisense oligonucleotides. Nucleic acid derivatives, as used herein, include chemically modified nucleic acids and nucleic acids containing chemically modified nucleotides. As used herein, reference to nucleic acids to be delivered using the disclosed compositions is intended to include nucleic acid derivatives. Preferred nucleic acids and nucleic acid derivatives for delivery to bacterial cells as a porphyrin composition are external guide sequences.

For conversion of drug-resistant eukaryotic cells to drug-sensitive eukaryotic cells, ribozymes, external guide sequences, or DNA encoding ribozymes or external guide sequences are used.

I. External Guide Sequences and Ribozymes

Ribonucleic acid (RNA) molecules can serve not only as carriers of genetic information, for example, genomic retroviral RNA and messenger RNA (mRNA) molecules and as structures essential for protein synthesis, for example, transfer RNA (tRNA) and ribosomal RNA (rRNA) molecules, but also as enzymes which specifically cleave nucleic acid molecules. Such catalytic RNA molecules are called ribozymes.

The use of catalytic RNA in commercial applications, particularly in therapeutics, is reviewed by Altman, *Proc.* *Natl. Acad. Sci. USA* 90:10898–10900 (1993); Symons, *Annu. Rev. Biochem.* 61:641–671 (1992); Rossi et al., *Antisense Res. Dev.,* 1:285–288 (1991); and Cech, *Annu. Rev. Biochem.* 59:543–568 (1990). Several classes of catalytic RNAs (ribozymes) have been described, including intron-derived ribozymes (WO 88/04300; see also, Cech, *Annu. Rev. Biochem.,* 59:543–568 (1990)), hammerhead ribozymes (WO 89/05852 and EP 321021 by GeneShears), axehead ribozymes (WO 91/04319 and WO 91/04324 by Innovir), as well as RNAase P.

RNAase P is a ribonucleoprotein having two components, an RNA component and a protein component. RNAase P is responsible for the cleavage which forms the mature 5' ends of all transfer RNAs. The RNA component of RNAase P is catalytic. RNAase P is endogenous to all living cells examined to date. During the studies on recognition of substrate by RNAase P, it was found that *E. coli* RNAase P can cleave synthetic tRNA-related substrates that lack certain domains, specifically, the D, T and anticodon stems and loops, of the normal tRNA structure. A half-turn of an RNA helix and a 3' proximal CCA sequence contain sufficient recognition elements to allow the reaction to proceed. The 5' proximal sequence of the RNA helix does not have to be covalently linked to 3' proximal sequence of the helix. The 3' proximal sequence of the stem can be regarded as a "guide sequence" because it identifies the site of cleavage in the 5' proximal region through a base-paired region.

Using these principles, any RNA sequence can be converted into a substrate for bacterial RNAase P by using an external guide sequence, having at its 5' terminus nucleotides complementary to the nucleotides 3' to the cleavage site in the RNA to be cleaved and at its 5' terminus the nucleotides NCCA (N is any nucleotide). This is described in U.S. Pat. No. 5,168,053, WO 92/03566 and Forster and Altman, *Science* 238:407–409 (1990).

EGS for promoting RNAase P-mediated cleavage of RNA has also been developed for use in eukaryotic systems as described by U.S. Pat. No. 5,624,824, Yuan et al., *Proc. Natl. Acad. Sci. USA* 89:8006–8010 (1992), WO 93/22434, WO 95/24489, WO 96/21731, and in U.S. application Ser. No. 08/615,961, filed Mar. 14, 1996. As used herein, "external guide sequence" and "EGS" refer to any oligonucleotide or oligonucleotide analog that forms, in combination with a target RNA, a substrate for RNAase P. EGS technology has been used successfully to decrease levels of gene expression in both bacteria (Altman et al. (1993)) and mammalian cells in tissue culture (Yuan et al., *Proc. Natl. Acad. Sci. USA* 89:8006–8010 (1992); Liu and Altman, *Genes Dev.* 9:471–480 (1995)).

The ability of EGS molecules to target and promote RNAase P activity is readily determined using an in vitro activity assay for cleavage by RNAase P of a target RNA sequence. In the case of EGS molecules with modified nucleotides or nucleotide linkages, a stability assay allows determination of the nuclease resistance of various types of modification. The activity assay permits comparison of the efficiency of RNAase P-mediated cleavage promoted by EGS molecules with different modifications. Together, the assays can be used to optimize and balance stability and cleavage efficiency of modified EGS molecules.

Cleavage of a target RNA by a ribozyme can be made most efficient by choosing target sites in the target RNA that are most accessible. Techniques for identifying such sites are described in U.S. Pat. Nos. 5,525,468 and 5,496,698.

a. Prokaryotic External Guide Sequences

The requirements for a EGS functional with prokaryotic RNAase P are less stringent than those for a eukaryotic EGS.

The critical elements of a prokaryotic EGS are (1), nucleotide sequence which specifically binds to the targeted RNA substrate to produce a short sequence of base pairs 3' to the cleavage site on the substrate RNA and (2) a terminal 3'-NCCA, where N is any nucleotide, preferably a purine. The sequence generally has no fewer than four, and more usually six to fifteen, nucleotides complementary to the targeted RNA. It is not critical that all nucleotides be complementary, although the efficiency of the reaction will vary with the degree of complementarity. The rate of cleavage is dependent on the RNAase P, the secondary structure of the hybrid substrate, which includes the targeted RNA and the presence of the 3'-NCCA in the hybrid substrate. Eukaryotic external guide sequences, preferred examples of which are described below, also promote cleavage by prokaryotic RNAase P and can be used for this purpose.

b. Eukaryotic External Guide Sequences

An external guide sequence for promoting cleavage by eukaryotic RNAase P, referred to herein as a eukaryotic EGS, contains sequences which are complementary to the target RNA and which forms secondary and tertiary structure akin to portions of a tRNA molecule. A preferred form of eukaryotic EGS contains at least seven nucleotides which base pair with the target sequence 3' to the intended cleavage site to form a structure like the amino acyl acceptor stem (A stem), nucleotides which base pair to form a stem and loop structure similar to the T stem and loop, followed by at least three nucleotides that base pair with the target sequence to form a structure like the dihydroxyuracil stem. Another preferred form of eukaryotic EGS, referred to herein as a Short External Guide Sequence (SEGS), provide a minimal structure recognized as a substrate by RNAase P when hybridized to a target molecule. The SEGS/target RNA complex includes structures similar to the A stem and the T stem of a tRNA, the natural substrate of RNAase P.

i. Design of Eukaryotic External Guide Sequences

Preferred guide sequences for eukaryotic RNAase P consist of a sequence which, when in a complex with the target RNA molecule, forms a secondary structure resembling that of a tRNA cloverleaf or a part of it. As used herein, the term "resembling a precursor tRNA" means a complex formed by the EGS with target RNA substrate to resemble a sufficient portion of the tRNA secondary and tertiary structure to result in cleavage of the target RNA by RNAase P. The sequence of the EGS can be derived from any tRNA except that the D stem and aminoacyl stem have to be altered to be complementary to the target substrate sequence. These altered stems are referred to as recognition arms. The recognition arm corresponding to the aminoacyl stem is referred to as the A recognition arm and the recognition arm corresponding to the D stem is referred to as the D recognition arm. The complementary sequences may consist of as few as seven nucleotides, but preferably include eleven nucleotides, in two blocks (the A and D recognition arms) which base pair with the target sequence and which are preferably separated by two unpaired nucleotides in the target sequence, preferably UU, wherein the two blocks are complementary to a sequence 3' to the site targeted for cleavage.

Figure 3:
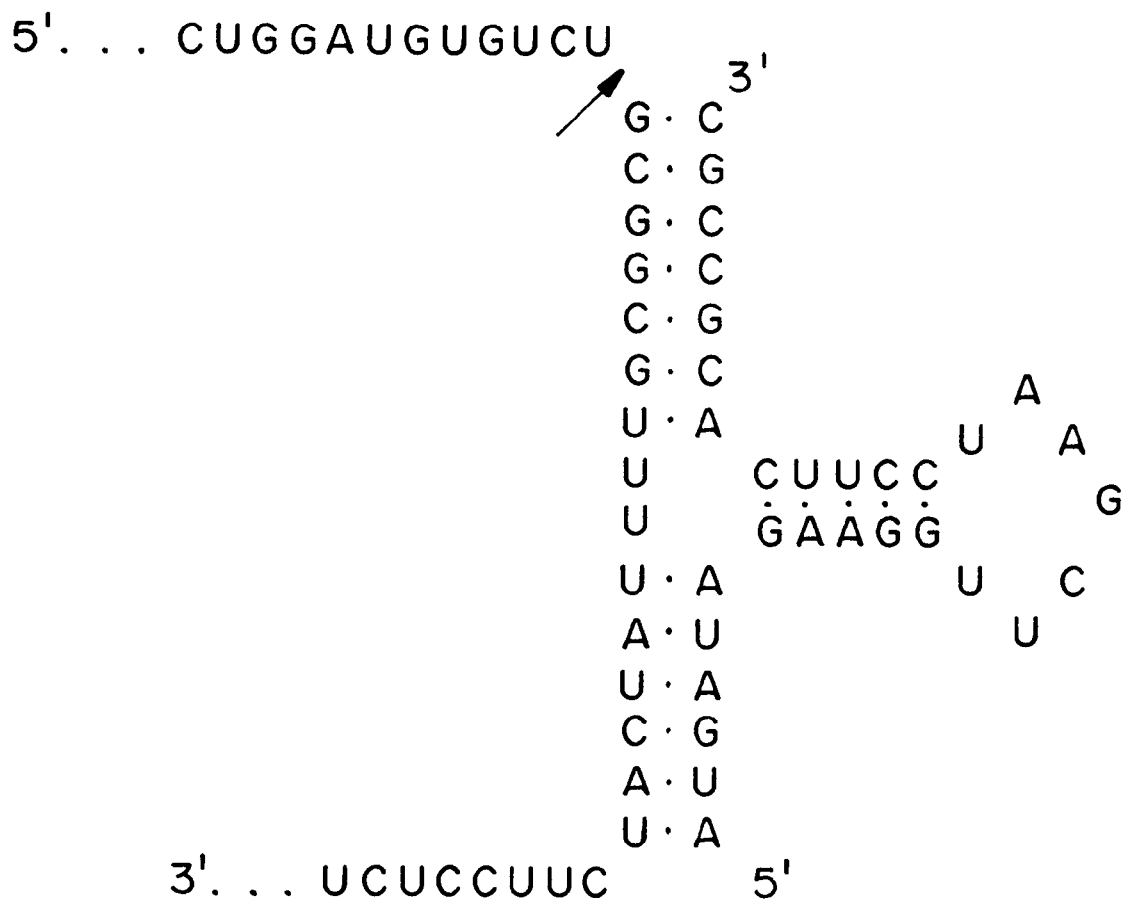
FIG. 3 is a diagram of the structure of an example of an external guide sequence (SEQ ID NO:3) hybridized to a target RNA molecule (nucleotides 1 to 35 of SEQ ID NO:1). The EGS includes a D recognition arm, an A recognition arm, and a region forming a structure similar the T stem and loop of a tRNA.

The remaining portion of the guide sequence, which is required to cause RNAase P catalytic RNA to interact with the EGS/target sequence complex, is herein referred to as an RNAase P binding sequence. The anticodon loop and stem and extra loop can be deleted and the sequence of the T loop and stem can be changed without decreasing the usefulness of the guide sequence and, in the case of the anticodon stem and loop deletion, increases the efficiency of the reaction by about ten fold. An example of a eukaryotic external guide sequence in association with a target RNA molecule is shown in FIG. 3. External guide sequences can also be derived using in vitro evolution techniques. Example of this are described in U.S. Pat. No. 5,624,824 and WO 95/24489.

The desired secondary structure is determined using conventional Watson-Crick base pairing schemes to form a structure resembling a tRNA, that is, having structure as described below. The specific sequence of the hydrogen bonded regions is less critical than the desired structure to be formed.

ii. Design of Short EGS Molecules

Figure 4:
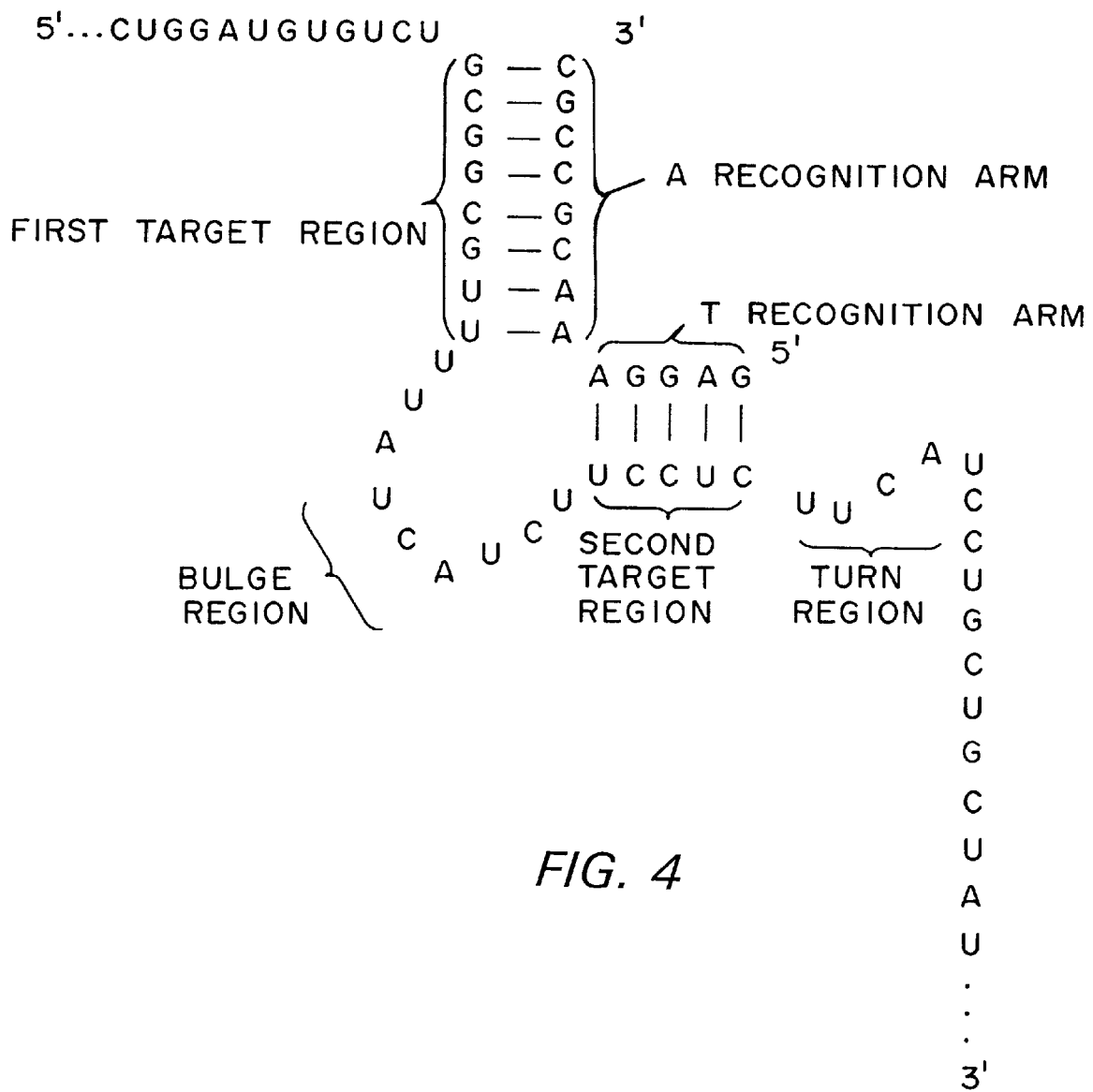
FIG. 4 is a diagram of the structure of an example of a Short External Guide Sequence (SEQ ID NO:2) hybridized to a target RNA molecule (SEQ ID NO:1). The parts of the Short External Guide Sequence (SEGS) are, from 5' to 3', the T recognition arm and the A recognition arm. The parts of the target RNA are, from 5' to 3', the first target region, the bulge region, the second target region, and the turn region.

Short external guide sequence (SEGS) molecules can be designed by adapting a portion of the basic structure of a tRNA molecule to form a substrate recognition sequence. This recognition sequence is complementary to regions of a targeted sequence in a target RNA molecule. In SEGS, the recognition sequence is composed of two recognition arms, referred to as the A recognition arm and the T recognition arm, which, in combination with regions of the targeted sequence in the target RNA, form structures similar to the A stem and T stem, respectively, of a tRNA molecule. The T recognition arm is located 5' of and adjacent to the A recognition arm. The sequence of the recognition arms are chosen to be specifically complementary to two regions of the targeted sequence in the target RNA, referred to as the first target region and the second target region. The first target region encompasses, or is adjacent to and 3' of, the site where RNAase P-mediated cleavage occurs. An example of a SEGS associated with a target RNA is shown in FIG. 4. By allowing the target molecule to form more of the RNAase P substrate structure, SEGS molecules can be quite short. This makes SEGS molecules especially useful as therapeutic agents since they are easier and less expensive to manufacture and administer in quantity.

The sequences of the recognition arms are chosen such that the first and second target regions in the target RNA are separated by a short unpaired region, referred to as the bulge region. Formation of this structure is the only essential requirement for defining the nucleotide sequence of a SEGS. However, it is preferred that the sequences of the recognition arms are also chosen such that a UNR motif is present in the target RNA molecule adjacent to and 3' of the second target region. The UNR motif can be immediately adjacent to the second target region, or it may be separated from the second target region by one or a few spacer nucleotides. It is preferred that the UNR motif is separated from the second target region by from zero to ten spacer nucleotides, more preferred that the UNR motif is separated from the second target region by from zero to three spacer nucleotides, and most preferred that the UNR motif is separated from the second target region by one spacer nucleotide. The UNR motif has a nucleotide sequence of UNR where N represents any nucleotide, R represents any purine nucleotide, and U represents a uridine nucleotide. The region of the targeted sequence in the target RNA molecule that makes up the UNR motif, if present, and spacer nucleotides is referred to as the turn region. The turn region is immediately adjacent to and 3' of the second target region. Without wishing to be limited by any particular theory, it is believed that the potential of the turn region of the targeted sequence in a target RNA to form a uridine turn structure (see Quigley, and Rich, *Science* 194:796–806 (1976), and Junker and Pardi, *RNA* 1:219–222 (1995)) aids in promoting RNAase P-mediated cleavage of the target RNA.

According to the relationships described above, the targeted sequence in the target RNA is composed of, from 5' to 3', the first target region, the bulge region, and the second target region, where the A recognition arm of the SEGS is complementary to the first target region and the T recognition arm of the SEGS is complementary to the second target region. It is preferred that a turn region, preferably having a UNR motif, is also present in the targeted sequence 3' of the second target region.

The recognition arms can be any length that results in a functional SEGS molecule. It is preferred that the A recognition arm and T recognition arm together total from 12 to 16 nucleotides. It is most preferred that the A recognition arm and T recognition arm together total 12 or 13 nucleotides. In general, it is preferred that the A recognition arm be from seven to nine nucleotides long, and that the T recognition arm be from five to seven nucleotides long. It is most preferred that the A recognition arm be seven or eight nucleotides long and the T recognition arm be five or six nucleotides long. In general, the recognition arms can have any nucleotide sequence. As discussed below, the choice of sequence is preferably based on the sequence of a targeted sequence in a target RNA of interest. It is preferred that the nucleotide at the 3' end of the A recognition arm is a cytidine or guanidine nucleotide. It is most preferred that the nucleotide at the 3' end of the A recognition arm is a cytidine nucleotide.

The bulge region can be any length that results in a functional SEGS molecule. It is preferred that the bulge region be from 1 to 30 nucleotides long. It is more preferred that the bulge region be from five to fifteen nucleotides long. It is most preferred that the bulge region be nine nucleotides long. The turn region can have any sequence that results in a functional SEGS molecule.

The nucleotide sequences of the turn region are denoted herein using standard nucleotide base symbols. For reference, N represents any nucleotide, R represents any purine nucleotide, Y represents any pyrimide nucleotide, A represents an adenine nucleotide, C represents a cytosine nucleotide, G represents a guanine nucleotide, T represents a thymine nucleotide, and U represents a uracil nucleotide. It is preferred that the turn region has a sequence of NUNR. It is more preferred that the turn region has a sequence of NUCR or UUNR. It is most preferred that the turn region has a sequence of UUCR.

It is preferred that the turn region of a targeted sequence in a target RNA comprises a nucleotide sequence encompassed by the formula NNNR. It is more preferred that the turn region of a targeted sequence in a target RNA comprises a nucleotide sequence encompassed by at least one of the formulas NNYR, YNNR, or NYNR. It is still more preferred that the turn region of a targeted sequence in a target RNA comprises a nucleotide sequence encompassed by at least one of the formulas YNYR, NYYR, or YYNR. It is still more preferred that the turn region of a targeted sequence in a target RNA comprises a nucleotide sequence encompassed by at least one of the formulas YYYR, YUNR, or NUYR. It is still more preferred that the turn region of a targeted sequence in a target RNA comprises a nucleotide sequence encompassed by at least one of the formulas UYYR or YYCR, or at least one of the formulas YUYR, UUNR, or NUCR. It is still more preferred that the turn region of a targeted sequence in a target RNA comprises a nucleotide sequence encompassed by the formula UYCR, or at least one of the formulas UUYR or YUCR. It is most preferred that the turn region of a targeted sequence in a target RNA comprises a nucleotide sequence encompassed by the formula UUCR.

Where the turn region of a targeted sequence in a target RNA comprises a nucleotide sequence encompassed by the formula NNNY, it is preferred that the turn region comprises a nucleotide sequence encompassed by the formula YNNY. It is more preferred that the turn region of a targeted sequence in a target RNA comprises a nucleotide sequence encompassed by at least one of the formulas YNYY or YYNY. It is still more preferred that the turn region of a targeted sequence in a target RNA comprises a nucleotide sequence encompassed by the formula YYYY. It is still more preferred that the turn region of a targeted sequence in a target RNA comprises a nucleotide sequence encompassed by the formula YUYY or the formula UYCY. It is still more preferred that the turn region of a targeted sequence in a target RNA comprises a nucleotide sequence encompassed by at least one of the formulas UUYY or YUCY. It is most preferred that the turn region of a targeted sequence in a target RNA comprises a nucleotide sequence encompassed by the formula UUCY.

Functional SEGS molecules require only that they form, in combination with a target RNA, a structure corresponding to the A stem and T stem of precursor tRNA such that an unpaired region is present in the target RNA between the structures corresponding to the A stem and T stem of tRNA. No structure corresponding to the T loop of a tRNA is required. Thus, a functional SEGS molecule requires only a nucleotide sequence complementary to two regions of a target RNA molecule, where the regions of the target RNA molecule are separated by a region, the bulge region, that is not complementary to the SEGS. It is preferred that a turn region containing a UNR motif, or another preferred turn region nucleotide sequence as described above, is also present in the target RNA adjacent to and 3' of the structure corresponding to the T stem of tRNA.

SEGS can be designed to target any sequence in any target RNA of interest. However, SEGS are. preferably designed by searching the nucleotide sequence of a target RNA of interest for the location of UNR motifs, or another preferred turn region nucleotide sequence as described above. For more preferred SEGS, the search can be limited to the preferred sequences of turn regions as described above. Once a desired turn sequence is identified, the sequence of the T recognition arm of the SEGS is chosen to be complementary to nucleotides in the target RNA adjacent to and 5' of the turn region sequence, separated by one or a few spacer nucleotides, if desired. These nucleotides in the target RNA represent the second target region. The sequence of the A recognition arm of the SEGS is chosen to be complementary to nucleotides in the target RNA 5' of the second target region, separated by an unpaired region. The unpaired region is the bulge region in the targeted sequence.

c. Ribozymes

Ribozymes for use in the disclosed method include any trans-cleaving catalytic nucleic acid. Several classes of such ribozymes are known and have been either adapted or designed to cleave RNA molecules in a site-specific manner. In general, ribozymes having such endoribonuclease activity have been derived from self-cleaving RNA molecules by eliminating the site of cleavage from the self-cleaving RNA molecule and re-targeting cleavage to a target RNA molecule by modifying nucleotides in the self-cleaving RNA molecule to interact with the sequence of the target RNA molecule rather than the sequence of the eliminated cleavage site. The region of a ribozyme that interacts with the site of cleavage is referred to as a "guide sequence". For self-cleaving RNA molecules, and ribozymes derived from them, this guide sequence is part of the ribozyme molecule. Such guide sequences are referred to as "internal guide sequences" since they are internal to (that is, part of) the ribozyme. This is in contrast to external guide sequences which are not part of ribozyme molecules.

Intron-derived ribozymes are derived from self-excising introns found in *Tetrahymena* RNA. Design of ribozymes derived from *Tetrahymena* introns for the specific cleavage of target RNA molecules and their use is described in U.S. Pat. No. 4,987,071, WO 88/04300, and Cech, *Annu. Rev. Biochem.* 59:543–568 (1990). Hammerhead ribozymes are derived from self-cleaving RNA molecules present in certain viruses. The cleavage activity resides in a region of conserved secondary structure which resembles the head of a hammer (Buzayan et al., *Proc. Natl. Acad. Sci. USA* 83:8859–8862 (1968); Forster and Symons, *Cell* 50:9–16 (1987)). Design of hammerhead ribozymes for the specific cleavage of target RNA molecules and their use is described in U.S. Pat. No. 5,254,678, WO 89/05852, EP 321021, and U.S. Pat. No. 5,334,711. Derivatives of hammerhead ribozymes are described in U.S. Pat. No. 5,334,711; WO 94/13789; and WO 97/18312. Such derivatives, especially those containing chemically modified nucleotides, are particularly preferred for use in the disclosed compositions. Axehead ribozymes are derived from self-cleaving domains in some viroid RNAs. These domains are involved in cleavage of tandemly repeated viroid genomes generated during viroid replication. Design of axehead ribozymes for the specific cleavage of target RNA molecules and their use is described in U.S. Pat. No. 5,225,337, WO 91/04319, and WO 91/04324. Ribozymes for use in the disclosed method can also be produced using in vitro evolution techniques. Such techniques are described in WO 95/24489 and U.S. Pat. No. 5,580,967.

i. Ribonuclease P

Ribonuclease P is an enzyme consisting of protein and RNA subunits that cleaves tRNA precursors to generate the 5' termini of tRNAs. This essential enzymatic activity has been found in all cell types examined, both prokaryotic and eukaryotic. During the studies on recognition of substrate by RNAase P, it was found that *E. coli* RNAase P can cleave synthetic tRNA-related substrates that lack certain domains, specifically, the D, T and anticodon stems and loops, of the normal tRNA structure. A half-turn of an RNA helix and a 3' proximal CCA sequence contain sufficient recognition elements to allow the reaction to proceed. The 5' proximal sequence of the RNA helix does not have to be covalently linked to 3' proximal sequence of the helix. The 3' proximal sequence of the stem can be regarded as a "guide sequence" because it identifies the site of cleavage in the 5' proximal region through a base-paired region.

RNAase P from *E. coli* and human cells have similar but not identical biochemical properties. Their RNA components have similar secondary structures. However, the substrate range of human RNAase P is narrower than that of the *E. coli* enzyme. For example, although *E. coli* RNAase P can cleave a synthetic tRNA-related substrate that lacks three specific domains of the normal tRNA structure, the human enzyme and the structurally similar enzyme from the yeast, *S. cerevisiae*, cannot cleave the same substrate. However, the *E. coli* RNAase P can cleave a synthetic tRNA-related substrate that is also cleaved by the human RNAase P. Altman et al., *Genomics* 18:419–422 (1993), describes several mammalian RNAase P catalytic RNAs and identifies common features and differences.

As used herein for ease of convenience, RNAase P refers to the ribonucleoprotein consisting of prokaryotic or eukaryotic analogues of the *E. coli* protein subunit C5 protein and M1 RNA, regardless of source, whether isolated, or produced by chemical synthesis. The RNA subunit of RNAase P also can be transcribed from a gene. The eukaryotic RNAase P RNA subunit is referred to as H1 RNA. The RNA subunit need not necessarily manifest catalytic activity in the absence of protein subunits in vitro. As used herein, unless otherwise specified, RNAase P refers to the RNAase P in the cell in which the RNA to be cleaved is located, whether endogenous or added to the cell.

RNAase P catalytic RNA can be used as a ribozyme with the disclosed method. RNAase P catalytic RNA must be used in combination with a guide sequence, since the catalytic RNA subunit of RNAase P does not contain an internal guide sequence in the manner of self-cleaving RNAs. An RNAase P catalytic sequence can be represented by a molecule like the entire H1 or M1 RNA molecule, any functionally equivalent molecule of prokaryotic or eukaryotic origin or derivation, or any portion thereof shown to have catalytic activity, either alone or in combination with a protein. Such a catalytic RNA is referred to herein as RNAase P catalytic RNA and its sequence is referred to as an RNAase P catalytic sequence. RNAase P catalytic RNA can be derived from naturally occurring RNAase P catalytic RNAs, for example, by deleting portions and by making nucleotide substitutions. Such derived catalytic RNAs need only retain enough of the catalytic activity of naturally occurring RNAase P catalytic RNA to cleave target RNA. One method of generating RNAase P catalytic sequences is by in vitro evolution as described in WO 95/24489. An RNA as described above is considered an RNAase P catalytic RNA regardless of source, whether isolated, produced by chemical synthesis, or transcribed from a gene.

ii. RNAase P Internal Guide Sequences

An external guide sequence and RNAase P catalytic RNA can be used together as separate molecules, or they can be coupled together in a single molecule. In the latter case, the RNAase P catalytic RNA is given, in effect, an internal guide sequence. Such a combination, in a single oligonucleotide molecule, is referred to as an RNAase P internal guide sequence (RIGS). A RIGS can be used to cleave a target RNA molecule in the same manner as EGS. Design and use of RIGS are described in WO 95/24489.

RIGSs can be formed by coupling a guide sequence to an RNAase P catalytic sequence by any suitable means. For example, an EGS and RNAase P catalytic RNA can be prepared as separate molecules which are then covalently linked in vitro. A complete RIGS can be synthesized as a single molecule, either by chemical synthesis, or by in vitro or in vivo transcription of a DNA molecule encoding linked EGS and RNAase P catalytic sequence. The linkage between the EGS and RNAase P domains of an RIGS can have any form that allows the domains to cleave a target RNA. For example, the two domains could be joined by an oligonucleotide linker. Preferably, the linker will be composed of ordinary nucleotides joined by phosphodiester bonds. The EGS and RNAase P catalytic sequence components can be joined in either order, with the RNAase P catalytic sequence linked to either the 3' end or 5' end of the EGS component. When using a eukaryotic RIGS in the disclosed method, endogenous RNAase P proteins can interact with and stimulate activity of the RIGS.

d. Activity of EGS Molecules and Ribozymes

An in vitro cleavage assay which measures the percentage of target RNA remaining after incubation with various amounts of an EGS, in the presence of a non-limiting amount of RNAase P, or a ribozyme, can be used as an indicator of the potential activity of the EGS/RNAase P complex or ribozyme. EGS/RNAase P complexes or ribozymes that exhibit the highest in vitro activity are selected for further testing. The percentage of RNA remaining can be plotted as a function of the EGS or ribozyme concentration. The catalytic efficiency of an EGS/RNAase P or ribozyme can be expressed as $k_{cat}/K_m$ (where $k_{cat}$ is the rate constant of cleavage and $K_m$ is the Michaelis constant), the second order rate constant for the reaction of a free EGS or ribozyme and substrate RNA molecule. Following the methods of Heidenreich and Eckstein (*J. Biol. Chem.*, 267:1904–1909 (1992)), $k_{cat}/K_m$ is determined using the formula $$-\ln F/t = (k_{cat}/K_m)[C]$$

where F is the fraction of substrate left, t is the reaction time, and [C] is the EGS concentration.

e. Chemically Modified EGS and Ribozymes i. Types of Modifications

Although unmodified oligoribonucleotides can function as effective ribozymes and EGS in a nuclease-free environment, the short half-life in serum and inside cells can reduce their effectiveness. Chemical modifications can be made which greatly enhance the nuclease resistance of ribozymes and EGS without compromising their biological function of cleavage or promoting RNAase P-mediated cleavage of target RNA. In general, such modifications can be made at the 2' position of the nucleotides in a ribozyme or EGS, the 3' and 5' ends of a ribozyme or EGS, and in the phosphate linkages between the nucleotides in a ribozyme or EGS. For example, one or more of the nucleotides of an EGS construct can be replaced by 2' methoxy ribonucleotides, phosphorothioate deoxyribonucleotides, or phosphorothioate ribonucleotides using available nucleic acid synthesis methods. Modified nucleotides and oligonucleotides, and methods for their synthesis, are known. Some of these are described in Offensperger et al., *EMBO J.*, 12:1257–1262 (1993); WO 93/01286 by Rosenberg et al.; Agrawal et al., *Proc. Natl. Acad. Sci. USA*, 85:7079–7083 (1988); Sarin et al., *Proc. Natl. Acad. Sci. USA*, 85:7448–7794 (1989); Shaw et al., *Nucleic Acids Res*, 19:747–750 (1991); Orson et al., *Nucl. Acids Res.*, 19:3435–3441 (1991); Paolella et al., *EMBO J.*, 11:1913–1919 (1992); Pieken, et al., *Science*, 253:314–317 (1991); Heidenreich and Eckstain, *J. Biol. Chem*, 267:1904–1909 (1992); WO 91/17093 by Hybridon, Inc.; EP 0339842 by Ajinomoto Co., Inc.; WO 95/23225 by Ribozyme Pharmaceuticals, Inc.; WO 94/15619 by Johns Hopkins University; and U.S. Pat. No. 5,334,711 to Sproat et al.

In describing substituents used to modify nucleotides, oligonucleotides, ribozymes and EGS, alkyl or alkyl group refers to a saturated aliphatic hydrocarbon, including straight chain, branch chain, and cyclic alkyl groups. For this use it is preferred that such alkyl groups have 1 to 12 carbons. It is more preferred that such alkyl groups have 1 to 6 carbons. It is still more preferred that such alkyl groups have 1 to 2 carbons. It is most preferred that such alkyl groups have 1 carbon. These alkyl groups can also include one or more hydroxyl groups, one or more amino groups, or both. Such hydroxyl and amino groups can be coupled to any carbon atom in the alkyl group. As used herein, the term hydroxy alkyl is used to refer to an alkyl group including one or more hydroxyl groups, the term amino alkyl is used to refer to an alkyl group including one or more amino groups, and hydroxylamino alkyl is used to refer to an alkyl group including one or more hydroxyl groups and one or more amino groups. As used herein, allyl or allyl group refers to an unsaturated aliphatic hydrocarbon, including straight chain, branch chain, and cyclic alkyl groups. For this use it is preferred that such allyl groups have 1 to 12 carbons. It is more preferred that such allyl groups have 1 to 6 carbons. It is still more preferred that such allyl groups have 2 to 3 carbons. It is most preferred that such allyl groups have 3 carbons. Other substituents can also be used to modify the nucleotides, oligonucleotides and EGS described herein, such as aryl, alkaryl, and arylalkyl, where aryl refers to a benzyl group, alkaryl refers to an alkyl group substituted with an aryl group, and arylalkyl refers to an aryl group substituted with an alkyl group.

Use herein of the term modification in reference to nucleotides, oligonucleotides, ribozymes and EGS is intended to refer to chemical differences of a nucleotide or oligonucleotide relative to conventional nucleotides and oligonucleotides. Use of the term modification herein is not intended to limit the manner in which the modified nucleotides, oligonucleotides, ribozymes or EGS are produced. Similarly, references to replacing a chemical group on a nucleotide, oligonucleotide, ribozyme or EGS is intended to refer to chemical differences of a nucleotide or oligonucleotide relative to conventional nucleotides and oligonucleotides, and is not intended to limit the manner in which the nucleotides, oligonucleotides, ribozymes or EGS are produced.

Modifications at the 3' and 5' Ends

It is well documented in the current literature that degradation of oligonucleotide analogues is mainly attributable to 3'-exonucleases. Several studies have also demonstrated that various 3'-modifications can greatly decrease the nuclease susceptibility of these analogues. Thus, another method to reduce susceptibility to 3' exonucleases is introduction of a free amine to a 3' terminal hydroxyl group of the ribozyme or EGS molecule (see, for example, Orson et al., *Nucl. Acids Res.*, 19:3435–3441 (1991)). Another useful 3' terminal modification is to couple a thymine nucleotide to the end of a ribozyme or EGS with a 3' to 3' linkage. Such a structure is referred to herein as 3'-3'-thymine nucleotide or T(3'-3').

Preferred 3' modifications are those where the 3' hydroxyl of the ribozyme or external guide sequence is replaced with a chemical group such as —H, —O—$R^1$, —$NH_2$, —NH—$R^1$, —N—$R^1_2$, F, or -3'-nucleotide, where each $R^1$ is independently alkyl, hydroxy alkyl, amino alkyl, hydroxylamino alkyl, allyl, —$PR^2(O)$—$R^2$, or —$PR^2(S)$—$R^2$, where each $R^2$ is independently O, S, F, alkyl, hydroxy alkyl, amino alkyl, hydroxylamino alkyl, allyl, O—$R^3$, or S—$R^3$, and where each $R^3$ is independently alkyl, hydroxy alkyl, amino alkyl, hydroxylamino alkyl, or allyl. More preferred 3' modifications are those where the 3' hydroxyl of the external guide sequence is replaced with a chemical group such as —H, —O—$CH_3$, —$NH_2$, —NH—$CH_3$, —N—$(CH_3)_2$, F, -3'-thymine nucleotide, —OPO(O)—$CH_3$, —OPO(S)—$CH_3$, —OPO(O)O$CH_2$CH(OH)—$CH_2NH_2$, or —OPO(S) O$CH_2$CH(OH)—$CH_2NH_2$. The most preferred 3' modifications are those where the 3' hydroxyl of the ribozyme or external guide sequence is replaced with -3'-thymine nucleotide, —OPO(O)O$CH_2$CH(OH)—$CH_2NH_2$, or —OPO(S)O$CH_2$CH(OH)—$CH_2NH_2$. As used herein, the 3' hydroxyl of a EGS refers to the hydroxyl group that would normally be present on the 3' carbon of the ribose residue in the 3' terminal nucleotide of the EGS. As used herein, the 3' carbon of a ribozyme or EGS refers to the 3' carbon of the ribose residue in the 3' terminal nucleotide of the ribozyme or EGS.

Although it is preferred that the 5' end of ribozymes and EGS have a hydroxyl or phosphate group, the 5' end can be modified to increase resistance of the ribozyme or EGS to nucleases. Preferred 5' modifications are those where the 5' hydroxyl of the ribozyme external guide sequence is replaced with a chemical group such as —H, —O—$R^4$, —$NH_2$, —NH—$R^4$, —N—$R^4{}_2$, or F, where each $R^4$ is independently alkyl, hydroxy alkyl, amino alkyl, hydroxylamino alkyl, allyl, —$PR^5$(O)—$R^5$, or —$PR^5$(S)—$R^5$, where each $R^5$ is independently O, S, F, alkyl, hydroxy alkyl, amino alkyl, hydroxylamino alkyl, allyl, O—$R^6$, or S—$R^6$, and where each $R^6$ is independently alkyl, hydroxy alkyl, amino alkyl, hydroxylamino alkyl, or allyl. More preferred 5' modifications are those where the 5' hydroxyl of the external guide sequence is replaced with a chemical group such as —H, —O—$CH_3$, —$NH_2$, —NH—$CH_3$, —N—$(CH_3)_2$, F, —OPO(O)—$CH_3$, —OPO(S)—$CH_3$, —OPO(O)$OCH_2CH(OH)$—$CH_2NH_2$, or —OPO(S)$OCH_2CH(OH)$—$CH_2NH_2$. The most preferred 5' modifications are those where the 5' hydroxyl of the ribozyme or external guide sequence is replaced with —OPO(O)$OCH_2CH(OH)$—$CH_2NH_2$, or —OPO(S)$OCH_2CH(OH)$—$CH_2NH_2$. As used herein, the 5' hydroxyl of a ribozyme or EGS refers to the hydroxyl that would normally be present on the 5' carbon of the ribose residue in the 5' terminal nucleotide of the ribozyme or EGS to which a phosphate group would normally be attached. As used herein, the 5' carbon of a ribozyme or EGS refers to the 5' carbon of the ribose residue in the 5' terminal nucleotide of the ribozyme or EGS. Another useful modification is covalent attachment of an intercalating agent, such as an acridine derivative, to the 5' terminal phosphate (for example, using a pentamethylene bridge) (see, for example, Maher et al., *Science*, 245:725–730 (1989); Grigoriev et al., *J. Biol. Chem.*, 267:3389–3395 (1992)). WO 95/23225 describes chemical modifications for increasing the stability of ribozymes, such as the introduction of an alkyl group at the 5' carbon of a nucleoside or nucleotide sugar. Such modifications can also be used in EGS molecules.

Modifications at the 2' Position of Nucleotides

Another class of useful chemical modifications is modification of the 2' OH group of a nucleotide's ribose moiety, which has been shown to be critical for the activity of the various intracellular and extracellular nucleases. Typical 2' modifications are the synthesis of 2'-O-methyl oligonucleotides (Paolella et al., *EMBO J.*, 11:1913–1919, 1992) and 2'-fluoro and 2'-amino-oligonucleotides (Pieken, et al., *Science*, 253:314–317 (1991); Heidenreich and Eckstain, *J. Biol. Chem*, 267:1904–1909 (1992)). Ribozymes and EGS molecules can also contain deoxyribonucleotides. Such substitutions improve nuclease resistance by eliminating the critical 2' OH group. WO 95/23225 describes 2'-deoxy-2'-alkylnucleotides which may be present to enhance the stability of oligonucleotides.

Preferred 2' modifications are those where the 2' hydroxyl of a nucleotide is replaced with a chemical group such as —H, —O—$R^7$, —$NH_2$, —NH—$R^7$, —N—$R^7{}_2$, F, or -2'-nucleotide, where each $R^7$ is independently alkyl, hydroxy alkyl, amino alkyl, hydroxylamino alkyl, allyl, —$PR^8$(O)—$R^8$, or —$PR^8$(S)—$R^8$, where each $R^8$ is independently O, S, F, alkyl, hydroxy alkyl, amino alkyl, hydroxylamino alkyl, allyl, O—$R^9$, or S—$R^9$, and where each $R^9$ is independently alkyl, hydroxy alkyl, amino alkyl, hydroxylamino alkyl, or allyl. More preferred 2' modifications are those where the 2' hydroxyl of a nucleotide is replaced with a chemical group such as —H, —O—$CH_3$, —$NH_2$, —NH—$CH_3$, —N—$(CH_3)_2$, F, —$OCH_2$—CH=$CH_2$, —OPO(O)—$CH_3$, or —OPO(S)—$CH_3$. The most preferred 2' modification is where the 2' hydroxyl of a nucleotide is replaced with —O—$CH_3$.

Modifications to the Phosphate Linkages

Modification to the phosphate groups linking nucleotides in a ribozyme or EGS can also be used to enhance the resistance of the ribozyme or EGS to nucleases. Typical modification for this purpose include replacing one or both of the free oxygen atoms with sulfur or a halogen. The free oxygen atoms, or a sulfur atom, if present, can also be linked to chemical groups such as alkyl, hydroxy alkyl, amino alkyl, hydroxylamino alkyl, or allyl. Examples of such substitutions, such as the use of 3' and/or 5' dihalophosphonate substituted nucleotides (for example, 3' and/or 5'-$CF_2$-phosphonate substituted nucleotides), are described in WO 95/23225. Preferred modified phosphate linking groups for use in EGS include —$OPR^{10}$(O)O—, —$OPR^{10}$(S)O—, and —OPO(S)O—, where $R^{10}$ is alkyl, hydroxy alkyl, amino alkyl, hydroxylamino alkyl, allyl, —O—$R^{11}$, —$NH_2$, —NH—$R^{11}$, —N—$R^{11}{}_2$, or F, and where $R^{11}$ is alkyl, hydroxy alkyl, amino alkyl, hydroxylamino alkyl, or allyl. More preferred modified phosphate linking groups for use in ribozymes and EGS include —$OPR^{12}$(O)O—, —$OPR^{12}$(S)O—, and —OPO(S)O—, where $R^{12}$ is —$CH_3$, —O—$CH_3$, —$OCH_2$—CH=$CH_2$, —$NH_2$, —NH—$CH_3$, —N—$(CH_3)_2$, or F. The most preferred modified phosphate linking group for use in ribozymes and EGS is —OPO(S)O—, which is commonly referred to as a phosphorothioate.

Another useful modification is methylation of cytosine bases that may be present in the sequence. The stability of ribozyme/target RNA hybrids or EGS/target RNA hybrids can be increased by using modified nucleotides that result in oligonucleotides with stronger base pairing to the target RNA. For example, C-5 propynyl pyrimide nucleotides increase hydrogen bonding between nucleic acids (Froehler et al., *Tetrahedron Letters* 33:5307–5310 (1992)).

The extent to which modifications affect the efficiency with which a modified ribozyme cleaves, or a modified EGS molecule promotes ribozyme-mediated cleavage of, target RNA can readily be determined using the cleavage assay described above.

ii. Chimeric Ribozymes and EGS Molecules

The above modifications can be used in limited regions of the ribozyme or EGS molecules and/or in combinations to result in chimeras of modified ribozymes and EGS molecules. Certain regions of ribozymes and EGS molecules are more amenable to modification than others due to the requirement for proper nucleotide interactions to form an active three-dimensional structure. For example, it has been discovered that incorporation of 2'-O-methyl nucleotides and phosphorothioate linkages can be introduced into certain regions of an EGS without a significant loss of RNAase P targeting activity. It has also been discovered that 2'-O-methyl ribonucleotides can replace any nucleotides in the sequences complementary to the target sequences and in the T stem. Accordingly, it is preferred that all of the nucleotides in the sequences complementary to the target sequences and in the T stem be replaced with nucleotides modified at the 2' position, and most preferred that the nucleotides be replaced with 2'-O-methyl ribonucleotides.

Only a portion of the nucleotides in the T loop can be replaced with 2'-O-methyl nucleotides without significantly affecting ribozyme cleavage. For maximum ribozyme cleavage activity, it is preferred that all of the nucleotides in the T loop portion of an EGS molecule comprise either unmodified ribonucleotides or ribonucleotides having phosphorothioate linkages, and most preferred that all of the nucleotides in the T loop portion of an EGS molecule comprise unmodified ribonucleotides having phosphate linkages. For balancing stability against nuclease digestion and ribozyme cleavage activity, it is preferred that pyrimidine nucleotides in the T loop portion of an EGS molecule be replaced by purine ribonucleotides, 2'-O-modified ribonucleotides, deoxyribonucleotides, or a combination. It is also preferred that the nucleotides in the T loop portion of an EGS molecule comprise a combination of ribonucleotides, 2'-O-modified ribonucleotides, and deoxyribonucleotides. It is also preferred that the nucleotides in the T loop portion of an EGS molecule comprise a combination of 2'-O-modified ribonucleotides and deoxyribonucleotides. It is particularly preferred that the T loop portion of an EGS comprise 2'-O-modified guanine ribonucleotides, adenine ribonucleotides, and uridine deoxyribonucleotides.

The extent to which modifications affect the efficiency with which the modified ribozyme or EGS molecule promotes RNAase P-mediated cleavage of a target RNA can readily be determined using the cleavage assay described above. Chemically modified ribozymes and EGS molecules can be classified according to the level of ribozyme cleavage activity of the modified ribozyme, or mediated by the modified EGS, when compared with the ribozyme cleavage activity of an unmodified ribozyme, or ribozyme cleavage activity mediated by an unmodified EGS, where an unmodified ribozyme or EGS molecule is a ribozyme or EGS molecule having the same nucleotide sequence as the modified ribozyme or EGS, respectively, but which is comprised of unmodified ribonucleotides, unmodified phosphodiester linkages, and unmodified 3' and 5' ends. This comparison provides the relative ribozyme cleavage activity of the modified ribozyme or EGS molecule, which is preferably expressed as a percentage of the ribozyme cleavage activity of the unmodified ribozyme or EGS molecule. Modified ribozymes and EGS molecules can be divided into classes based on these activity levels. In this way, modified EGS molecules can be divided, for example, into four classes: (1) modified EGS molecules mediating greater than 70% of the ribozyme cleavage activity mediated by an unmodified EGS, (2) modified EGS molecules mediating from 50% to 70% of the ribozyme cleavage activity mediated by an unmodified EGS, (3) modified EGS molecules mediating from 25% to 50% of the ribozyme cleavage activity mediated by an unmodified EGS, and (4) modified EGS molecules mediating less than 25% of the ribozyme cleavage activity mediated by an unmodified EGS. Preferred modified EGS molecules mediate at least 25% of the ribozyme cleavage activity mediated by an unmodified EGS. More preferred EGS molecules mediate at least 50% of the ribozyme cleavage activity mediated by an unmodified EGS. The most preferred EGS molecules mediate at least 70% of the ribozyme cleavage activity mediated by an unmodified EGS. Similarly, modified ribozymes can be divided, for example, into four classes: (1) modified ribozymes having greater than 70% of the ribozyme cleavage activity of an unmodified ribozyme, (2) modified ribozymes having from 50% to 70% of the ribozyme cleavage activity of an unmodified ribozyme, (3) modified ribozymes having from 25% to 50% of the ribozyme cleavage activity of an unmodified ribozyme, and (4) modified ribozymes having less than 25% of the ribozyme cleavage activity of an unmodified ribozyme. Preferred modified ribozymes have at least 25% of the ribozyme cleavage activity of an unmodified ribozyme. More preferred ribozymes have at least 50% of the ribozyme cleavage activity of an unmodified ribozyme. The most preferred ribozymes have at least 70% of the ribozyme cleavage activity of an unmodified ribozyme.

Fetal Calf Serum Stability Assay

The nuclease resistance of chemically modified ribozymes and EGS molecules can be tested in a Fetal Calf Serum (FCS) Assay. It was reported by Shaw et al., *Nucleic Acids Res.* 19:747–750 (1991), that 10% FCS, when heated inactivated, mimics rather closely the human serum. The assay conditions are very similar to that previously described by Hoke et al., *Nucleic Acids Res.* 19:5743–5748 (1991). Briefly, a ribozyme or EGS to be tested is 5'-end labeled with T4 polynucleotide kinase and [γ-$^{35}$S] ATP (this procedure can generate radiolabeled oligonucleotides which are resistant against dephosphorylation). The labeled ribozyme or EGS is then purified by phenol/chloroform extraction, followed by a Sephadex G-25 spin-column filtration. The purified ribozyme or EGS is mixed with unlabeled ribozyme or EGS and 10% heat-inactivated fetal calf serum (FCS) so that the final concentration of ribozyme or EGS is about 5 μM. Ribozymes and EGS are treated over a period of 24 hours. Aliquots are withdrawn from the reaction mixture at different time points, mixed with 2× loading dye, heat inactivated at 90° C. for 3 minutes, then stored at −20° C. The results can be analyzed on 12% polyacrylamide/7 M urea gels.

f. Method for Producing EGSs and Ribozymes Having Enhanced Efficacy

EGSs and ribozymes having enhanced binding affinity as measured by decreased energy of binding can be designed by in vitro evolution. Such a method can be used to identify RNA molecules with desired properties from pools of molecules that contain randomized sequences. This selection scheme is described in PCT application WO 95/24489 by Yale University. In each round of selection, the pool of RNAs is digested with human RNAase P, or with the ribozyme, and the cleaved products are isolated by electrophoresis and then amplified to produce progeny RNAs. One of the template-creating oligonucleotides is used as the 5' primer for the polymerase chain reaction (PCR) in order to allow restoration of the promoter sequence and the leader sequence of the chimeric RNA for the next cycle of selection. The stringency of selection is increased at each cycle by reducing the amount of enzyme and the time allowed for the cleavage reaction, such that only those substrates that are cleaved rapidly by the enzyme are selected.

In the first three rounds of selection, RNA substrates are digested with an appropriate amount of human RNAase P, for example, 3.6 units, or the equivalent activity of the ribozyme. One unit of human RNAase P is defined as that amount of enzyme that cleaves 1 pmol of precursor to tRNA$^{Tyr}$ from *E. coli* in 30 min at 37° C. For assays in subsequent rounds of selection, the amount of enzyme can be reduced, and the incubation time can be shortened so that less than 20 percent of the substrate is cleaved. Cleavage products are separated from uncleaved substrates by electrophoresis and RNA extracted.

The purified cleavage product RNAs are reverse transcribed and amplified by PCR. The double-stranded DNA generated by PCR regains the promoter sequence and the leader sequence from the sequence in the primer, and is then used as a template for transcription of RNA for the next round of selection. After several cycles of selection, the resulting pool of double-stranded DNAs can be cloned into an appropriate vector and sequenced.

In order to test the activities of EGSs or ribozymes derived from the individual variants, sequences corresponding to the EGS or ribozyme segment of each chimeric RNA can be amplified by PCR, and RNAs transcribed with an appropriate RNA polymerase. RNA cleavage by the selected EGS or ribozyme is then assayed. Sequences in common in the most active EGS and ribozymes are then determined and new EGS and ribozymes designed.

g. Synthesis of EGS and Ribozymes

Oligonucleotides having known sequences can be routinely synthesized using automated nucleic acid synthesis, for example, using the cyanoethyl phosphoramidite method on a DNA model 392 synthesizer by Applied Biosystems, Inc. (Foster City, Calif.) or a Pharmacia Oligo Pilot (Pharmacia, Piscataway, N.J.). Other methods for synthesizing nucleic acid molecules are also available (see, for example, Ikuta et al., *Ann. Rev. Biochem.* 53:323–356 (1984) (phosphotriester and phosphite-triester methods); Narang et al., *Methods Enzymol.* 65:610–620 (1980) (phosphotriester method). These methods can be used to synthesize EGS molecules and ribozymes. Alternatively, EGS molecules or ribozymes can be synthesized by transcribing DNA templates, for example, with T7 RNA polymerase (Milligan et al., *Nucl Acids Res.* 15:8783 (1987)). EGS molecules and ribozymes can also be synthesized in cells by placing a vector that encodes and expresses the EGS in the cells.

C. Compositions For Delivery of Nucleic Acids to Bacterial Cells

Compositions for delivery of nucleic acids to prokaryotic cells are a combination of a macrocyclic compound and the nucleic acid. In the preferred embodiments, the macrocyclic compounds are porphyrins or phthalocyanins; in the most preferred embodiment, the porphyrins are water soluble. The nucleic acid to be delivered has a net overall negative charge; the macrocyclic compound has a net overall positive charge under physiological conditions. (that is, a pH of approximately 7.0 to 7.5, more typically 7.2 to 7.4). As a result, the nucleic acid to be delivered is ionically bound to the macrocyclic compound until it and the bound nucleic acids are internalized in the targeted cells. The nucleic acid to be delivered to prokaryotic cells can also be covalently coupled to a macrocyclic compound.

D. Compositions For Phenotypic Conversion of Eukaryotic Cells

EGS molecules and ribozymes can be used directly in combination with a pharmaceutically acceptable carrier to form a pharmaceutical composition suited for treating a patient. Alternatively, an EGS or ribozyme can be delivered to a eukaryotic cell via a vector containing a sequence which encodes and expresses the EGS molecule or ribozyme specific for a particular RNA.

A variety of carriers are available for delivering EGS molecules and ribozymes, or DNA encoding EGS molecules and ribozymes, to cells. For example, in general, the EGS molecules, ribozymes or DNA sequences encoding the EGS molecules or ribozymes, can be incorporated within or on microparticles. As used herein, microparticles include liposomes, virosomes, microspheres and microcapsules formed of synthetic and/or natural polymers. Methods for making microcapsules and microspheres are known to those skilled in the art and include solvent evaporation, solvent casting, spray drying and solvent extension. Examples of useful polymers which can be incorporated into various microparticles include polysaccharides, polyanhydrides, polyorthoesters, polyhydroxides and proteins and peptides.

Liposomes can be produced by standard methods such as those reported by Kim et al., *Biochim. Biophys. Acta,* 728:339–348 (1983); Liu et al., *Biochim. Biophys. Acta,* 1104:95–101 (1992); and Lee et al., *Biochim. Biophys. Acta.,* 1103:185–197 (1992); Wang et al., *Biochem.,* 28:9508–9514 (1989)). Nucleic acids to be delivered can be encapsulated within liposomes when the molecules are present during the preparation of the microparticles. Briefly, the lipids of choice, dissolved in an organic solvent, are mixed and dried onto the bottom of a glass tube under vacuum. The lipid film is rehydrated using an aqueous buffered solution of the nucleic acid molecules to be encapsulated, and the resulting hydrated lipid vesicles or liposomes encapsulating the material can then be washed by centrifugation and can be filtered and stored at 4° C. Alternatively, nucleic acid molecules can be incorporated within microparticles, or bound to the outside of the microparticles, either ionically or covalently.

Cationic liposomes or microcapsules are microparticles that are particularly useful for delivering negatively charged compounds such as nucleic acid-based compounds, which can bind ionically to the positively charged outer surface of these liposomes. Various cationic liposomes have previously been shown to be very effective at delivering nucleic acids or nucleic acid-protein complexes to cells both in vitro and in vivo, as reported by Felgner et al., *Proc. Natl. Acad. Sci. USA,* 84:7413–7417 (1987); Felgner, *Advanced Drug Delivery Reviews,* 5:163–187 (1990); Clarenc et al., *Anti-Cancer Drug Design,* 8:81–94 (1993). Cationic liposomes or microcapsules can be prepared using mixtures including one or more lipids containing a cationic side group in a sufficient quantity such that the liposomes or microcapsules formed from the mixture possess a net positive charge which will ionically bind negatively charged compounds. Examples of positively charged lipids that may be used to produce cationic liposomes include the aminolipid dioleoyl phosphatidyl ethanolamine (PE), which possesses a positively charged primary amino head group; phosphatidylcholine (PC), which possess positively charged head groups that are not primary amines; and N[1-(2,3-dioleyloxy)propyl]-N,N, N-triethylammonium ("DOTMA," see Felgner et al., *Proc. Natl. Acad. Sci USA,* 84:7413–7417 (1987); Felgner et al., *Nature,* 337:387–388 (1989); Felgner, *Advanced Drug Delivery Reviews,* 5:163–187 (1990)).

A preferred form of microparticle for delivery of nucleic acid molecules are heme-bearing microparticles. In these microparticles, heme is intercalated into or covalently conjugated to the outer surface of the microparticles. Heme-bearing microparticles offer an advantage in that since they are preferentially bound and taken up by cells that express the heme receptor, such as hepatocytes, the amount of drug or other compound required for an effective dose is significantly reduced. Such targeted delivery may also reduce systemic side effects that can arise from using relatively high drug concentrations in non-targeted delivery methods. Preferred lipids for forming heme-bearing microparticles are 1,2-dioleoyloxy-3-(trimethylammonium)propane (DOTAP) and dioleoyl phosphatidyl ethanolamine (DOPE). The production and use of heme-bearing microparticles are described in PCT application WO 95/27480 by Innovir, and Takle et al., *Antisense and Nucleic Acid Drug Dev.* 7:177–185 (1997). Nucleic acid can also be encapsulated by or coated on cationic liposomes which can be injected intravenously into a mammal.

For delivery to algal cells, protozoa, fungal cells, slime mold, or helminth cells infecting an animal, liposomes containing EGS molecules, ribozymes, or DNA encoding these molecules, can be administered systemically, for example, by intravenous or intraperitoneal administration. Other possible routes include trans-dermal or oral, when used in conjunction with appropriate microparticles. Generally, the total amount of the liposome-associated nucleic acid administered to an individual will be less than the amount of the unassociated nucleic acid that must be administered for the same desired or intended effect. Delivery of nucleic acids using porphyrins is described below.

Compositions including various polymers such as the polylactic acid and polyglycolic acid copolymers, polyethylene, and polyorthoesters and the EGS molecules, ribozymes, or DNA encoding such molecules, can be delivered locally to the appropriate cells by using a catheter or syringe. Other means of delivering such compositions locally to cells include using infusion pumps (for example, from Alza Corporation, Palo Alto, Calif.) or incorporating the compositions into polymeric implants (see, for example, Johnson and Lloyd-Jones, eds., *Drug Delivery Systems* (Chichester, England: Ellis Horwood Ltd., 1987), which can effect a sustained release of the therapeutic nucleic acid compositions to the immediate area of the implant.

Nucleic acids, such as ribozymes, external guide sequences, and vectors encoding ribozymes or external guide sequences, can also be delivered to eukaryotic cells using macrocyclic compounds as described in PCT application WO95/27480. In preferred embodiments, the macrocyclic compounds are porphyrins or phthalocyanins; in the most preferred embodiment, the porphyrins are water soluble. The nucleic acid to be delivered has a net overall negative charge; the macrocyclic compound has a net overall positive charge under physiological conditions, that is, pH of approximately 7.0 to 7.5, more typically 7.2 to 7.4. As a result, the nucleic acid to be delivered is ionically bound to the macrocyclic compound until it and the bound nucleic acids are internalized in the targeted cells.

E. Target Bacterial Cells For Delivery of Nucleic Acids

The method described herein for delivery of nucleic acids to bacterial cells can be applied to any desired species of bacteria. Preferred target bacteria are those that infect, colonize, or otherwise grow in or on plants or animals, including humans.

Preferred target bacterial cells are those that colonize, infect, or otherwise grow in or on animals. Particularly preferred are bacterial cells that colonize, infect, or grow in either or both the gastrointestinal tract or respiratory tract. Also preferred are bacterial cells that colonize, infect, or grow in the urogenital tract. Some preferred bacterial cells belong to one of the families Enterobacteriaceae, Micrococcaceae, Vibrionaceae, Pasteurellaceae, Mycoplasmataceae, or Rickettsiaceae. Within these families, preferred bacterial cells belong to one of the genera Salmonella, Shigella, Escherichia, Enterobacter, Serratia, Proteus, Yersinia, Citrobacter, Edwardsiella, Providencia, Klebsiella, Hafnia, Ewingella, Kluyvera, Morganella, Planococcus, Stomatococcus, Micrococcus, Staphylococcus, Vibrio, Aeromonas, Plessiomonas, Haemophilus, Actinobacillus, Pasteurella, Mycoplasma, Ureaplasma, Rickettsia, Coxiella, Agrobacterium, Phytopthera, Rochalimaea, or Ehrlichia. Particular preferred bacterial cells are those that belong to the family Enterobacteriaceae.

Preferred bacterial cells belong to one of the genera Salmonella, Shigella, Escherichia, Enterobacter, Serratia, Proteus, Yersinia, Citrobacter, Edwardsiella, Providencia, Klebsiella, Hafnia, Ewingella, Kluyvera, Morganella, Planococcus, Stomatococcus, Micrococcus, Staphylococcus, Vibrio, Aeromonas, Plessiomonas, Haemophilus, Actinobacillus, Pasteurella, Mycoplasma, Ureaplasma, Rickettsia, Coxiella, Rochalimaea, Ehrlichia, Streptococcus, Enterococcus, Aerococcus, Gemella, Lactococcus, Leuconostoc, Pedicoccus, Bacillus, Corynebacterium, Arcanobacterium, Actinomyces, Rhodococcus, Listeria, Erysipelothrix, Gardnerella, Neisseria, Camylobacter, Arcobacter, Wolinella, Heliobacter, Achomobacter, Acinetobacter, Agrobacterium, Alcaligenes, Chryseomonas, Comamonas, Eikenella, Flavimonas, Flavobacterium, Moraxella, Oligella, Pseudomonas, Skewanella, Weeksella, Xanthomonas, Bordetella, Franciesella, Brucella, Legionella, Afipia, Bartonella, Calymmatobacterium, Cardiobacterium, Streptobacillus, Spirillum, Peptostreptococcus, Peptococcus, Sarcinia, Coprococcus, Ruminococcus, Propionibacterium, Mobiluncus, Bifidobacterium, Eubacterium, Lactobacillus, Rothia, Clostridium, Bacteroides, Porphyromonas, Prevotella, Fusobacterium, Bilophila, Leptotrichia, Wolinella, Acidaminococcus, Megasphaera, Veilonella, Norcardia, Actinomadura, Norcardiopsis, Streptomyces, Micropolysporas, Thermoactinonycetes, Mycobacterium, Treponema, Agrobacterium, Phytopthera, Borrelia, Leptospira, or Chlamydiae.

Particularly preferred are bacterial cells that belong to one of the genera Salmonella, Shigella, Escherichia, Enterobacter, Serratia, Proteus, Yersinia, Citrobacter, Edwardsiella, Providencia, Klebsiella, Hafnia, Ewingella, Kluyvera, or Morganella. Most preferred are bacterial cells that belong to one of the genera Salmonella or Escherichia.

F. Target Eukaryotic Cells and Organisms for Phenotypic Conversion

The method described herein for phenotypic conversion can be applied to any eukaryotic cell that produces an RNA involved cell viability or in conferring drug resistance on the cell. The disclosed method can be used to convert drug-resistant cells to drug-sensitive cells, or to kill or reduce the viability of cells, in any setting. Preferred target eukaryotic cells are those that infect, colonize, or otherwise grow in or on plants or animals, including humans. Preferred target cells can harbor transmissible plasmids, episomal vectors, or viral vectors.

Preferred target cells are cells, and cells from organisms, that colonize, infect, or otherwise grow in or on animals. Particularly preferred are cells, and cells from organisms, that colonize, infect, or grow in blood, the gastrointestinal tract, and/or the respiratory tract. Also preferred are cells, and cells from organisms, that colonize, infect, or grow in the urogenital tract. Unless otherwise noted, references to cells for use as targets in the disclosed method are intended to include individual cells, cells isolated from an organism, and cells that are part of an organism. Similarly, reference to an organism as a target in the disclosed method is intended to mean that cells of the organism can be target cells in the disclosed method. Thus, for example, useful target cells for the disclosed method include cells of parasitic nematodes. In this case, it is preferred that the such cells be subjected to phenotypic conversion by delivery of the disclosed compositions to the organism.

Preferred pathogenic organisms, the cells of which are useful as targets of phenotypic conversion, include fungi, protozoa, and helminths. Preferred target organisms are ameba, flagellates, ciliates, sporozoa, coccidia, microsporidia, roundworms, flatworms, tapes, and flukes. Some preferred cells belong to one of the phyla Zygomycota, Dikaryomycota, Sarcomastigophora, Ciliophora, Apicomplexa, Microspora, Nematoda, and Platyhelminthes.

Preferred cells belong to one of the genera Candida, Trichosporan, Torulopsis, Pityrosporum, Epidermophytan, Coccidioides, Paracoccidioides, Entamoeba, Giardia, Dientainoeba, Balantidium, Isopora, Cryptosporidium, Enterocytozoon, Trichomas, Naegleria, Acanthamoeba, Plasmodium, Babesia, Toxoplasma, Leishmania, Trypanosoma, Pneumocystis, Enterobius, Ascaris, Toxocara, Trichuris, Ancylostoma, Necator, Strongyloides, Trichinella, Wuchereria, Brugia, Loa, Mansonella, Onchocerca, Dracunculus, Dirofiliaria, Fasciolopsis, Fasciola, Opisthorchis, Paragonimus, Schistosoma, Taenia, Diphyllobothtium, Echinococcus, Hymenolepsis, and Dipylidium. Preferred cells belong to one of the species *Entamoeba histolytica, Giardia lamblia, Dientamoeba fragilis, Balantidium coli, Isopora belli, Enterocytozoon bieneusi, Trichomas vaginalis, Toxoplasma gondii, Trypanosoma cruzi, Trypanosoma brucei, Trypanosoma congolense, Plasmodium falcipium, Plasmodium vivax, Pneumocystis carinii, Enterobius vermicularis, Ascaris lumbricoides, Trichuris trichiura, Ancylostoma duodenale, Necator americanus, Strongyloides stercoralis, Trichinella spiralis, Wuchereria bancrofti, Brugia malayi, Loa loa, Onchocerca volvulus, Dracunculus medinesis, Dirofiliaria immitis, Fasciolopsis buski, Fasciola hepatica, Opisthorchis sinensis, Paragonimus westermani, Taenia solium, Taenia saginata, Diphyllobothtium latum, Echinococcus granulosus, Echinococcus multilocaularis, Hymenolepsis nana, Hymenolepsis diminuta,* and *Dipylidium caninum.*

II. METHOD

A. Delivery of Nucleic Acids to Bacterial Cells

The disclosed porphyrin compositions can be used to deliver conjugated nucleic acid to bacterial cells. In general, delivery need only involve bringing the composition and the cell into contact. For example, the composition can be mixed with or applied to cells, including by addition to any liquid in which the bacteria are growing, as a liquid composition. Many modes and methods of delivery of compositions to bacteria are known and can be used with the disclosed compositions.

For delivery to bacteria in an animal or human, the disclosed porphyrin compositions will preferably be administered systemically, most typically orally or by intravenous or intraperitoneal injection, in an amount effective for delivery of the nucleic acid to the targeted cells. Other routes of administration that are useful include topical, transdermal, transmucosal and enteral. The disclosed compositions do not generally require any limited or specialized mode of administration or delivery.

In general, it is preferred that an effective amount of the conjugated nucleic acid be delivered to bacterial cells. Such an effective amount can depend on the therapeutic goal and the characteristics of the nucleic acid being delivered. For example, a preferred therapeutic goal is the alteration of expression of one or more bacterial genes by ribozyme cleavage of RNA transcribed from the gene(s). The effective amount in this case will generally depend on the activity of the ribozyme (or the cleavage mediated by an EGS) and its stability against nucleases. The effective amount is also dependent on whether the nucleic acid is a plasmid vector or a chemically-synthesized.

Although described primarily with reference to delivery of nucleic acids in vivo, it will be recognized by those skilled in the art that the same delivery system can be used for laboratory reagents for cell cultures and in diagnostic assays.

B. Phenotypic Conversion of Eukaryotic Cells

Eukaryotic pathogens can be killed or made less viable, and drug-resistant eukaryotic cells can be converted to drug-sensitive cells, by delivering EGS or ribozyme compositions to the cells. The ribozyme, external guide sequence, or nucleic acid encoding a ribozyme or external guide sequence can then cleave, or mediate cleavage of, a target RNA required for cell viability or involved in conferring drug resistance on the cell. In general, delivery need only involve bringing the composition and the cell into contact. Preferred target eukaryotic cells are those that infect, colonize, or otherwise grow in or on plants or animals, including humans. The disclosed method is preferably used to kill or convert the phenotype of fungi, most preferably fungal pathogens.

Two methods of delivery may be employed, (1) delivery of synthetic EGS or ribozyme molecules to the eukaryotic cells, or (2) delivery of a vector expressing EGS molecules or ribozymes to the eukaryotic cells. The method of choice can be determined by performing trials of the different methods, using standard methodology. The methods can also be used in combination. Both of them can be efficiently delivered, for example, by using cationic liposome preparations.

Direct delivery involves the insertion of pre-synthesized EGS molecules or ribozymes into the target cells, usually with the help of lipid complexes (liposomes) to facilitate the crossing of the cell membrane and other molecules, such as antibodies or other small ligands such as heme, to maximize targeting. Because of the sensitivity of RNA to degradation, in many instances, directly delivered EGS molecules or ribozymes may be chemically modified, making them nuclease resistant, as described above. This delivery methodology allows a more precise monitoring of the therapeutic dose.

Vector-mediated delivery involves introduction into the target cells of a self-replicating or a non-replicating system, such as a modified viral vector or a plasmid, which produces a large amount of the EGS or ribozyme encoded in a sequence carried on the vector. Targeting of the cells and the mechanism of entry may be provided by the virus, or, if a plasmid is being used, methods similar to the ones described for direct delivery of EGS molecules can be used. Vector-mediated delivery produces a sustained amount of EGS or ribozyme molecules. It is substantially cheaper and requires less frequent administration than a direct delivery such as intravenous injection of the EGS or ribozyme molecules. It is important that an effective amount of oligonucleotides be delivered in a form which minimizes degradation of the oligonucleotide before it reaches the intended target site. Viral vectors derived from viruses that normally infect the target cell are especially preferred for delivery of nucleic acid encoding EGS molecules and ribozymes.

For delivery to eukaryotic pathogens in an animal or human, the disclosed compositions are preferably administered systemically, most typically orally or by intravenous or intraperitoneal injection, in an amount effective for delivery of the nucleic acid to the targeted cells. Other routes of administration that are useful include topical, transdermal, transmucosal and enteral. The disclosed compositions do not generally require any limited or specialized mode of administration or delivery.

In general, it is preferred that an effective amount of the EGS or ribozyme composition be delivered to the eukaryotic cells. Such an effective amount can depend on the characteristics of the EGS, ribozyme, or vector encoding an EGS or ribozyme being delivered, such as the activity of the ribozyme (or the cleavage mediated by an EGS) and its stability against nucleases. The effective amount is also dependent on whether the nucleic acid is a ribozyme or EGS, or a vector encoding a ribozyme or EGS.

A preferred embodiment of the disclosed method involves the use of vectors, such as viral vectors, that can be transferred between eukaryotic cells through normal routes of infection. Such vectors can be adapted from viruses or plasmids that normally infect or are transferred between specific pathogenic cells or organisms. Vectors for eukaryotic cells and parasitic organisms are known. For example, Kelly et al., *Nucl. Acids Res.* 20:3963–3969 (1992), describe a vector for Trypanosoma and Leishmania.

For use for any animals or plants that harbor eukaryotic pathogens, a series of EGS molecules or ribozymes can be prepared in advance that are directed against a set of mRNAs encoded by various drug resistance genes and cloned into appropriate vectors. Sites of severe infections by drug-resistant eukaryotic cells can then be inoculated with cultures of cells harboring the set of "therapeutic" vectors and, after a suitable interval to allow for the vectors that encode the EGSs or ribozymes to be transmitted to the entire population, the appropriate drug can be administered to the animal or plant in which the pathogenic culture has now, presumably, been rendered drug sensitive. The precise method of "inoculation" (for example, aerosol, swab, enema, subcutaneous injection) may depend on the site of infection and the particular animal population being treated.

Mutation of the original drug-resistant cells to a novel form of resistance that prevents the EGS from exerting its effect on drug resistance phenotype is unlikely since a single base mismatch in the complex with the target mRNA will not significantly alter recognition by RNAase P (Kufel and Kirsebom, *Proc. Nat. Acad. Sci. USA* 93:6085–6090 (1996)).

The disclosed method and composition can also be used to convert the phenotype of drug-resistant eukaryotic pathogens of plants.

Many of the techniques described herein are known to those skilled in the art, as are methods for making, and sources of, reagents. The teachings of any references cited herein with respect to methods and reagents are specifically incorporated herein, as well as for the purpose of demonstrating the scope and level of skill in the art.

The present invention will be further understood by reference to the following non-limiting examples.

EXAMPLES

Example 1

Delivery of EGSs to Bacteria

This example demonstrates a preferred mode of enhancing the uptake of nucleic acids by bacteria and uses external guide sequences as the nucleic acid. An overnight *E. coli* culture was washed with 100 mM Tris-Cl pH 7.0 (TB) and suspended in TB to give an $OD_{623nm}$ of 1.0. Two hundred microliter solutions containing 5 $\mu$g EGS (with approximately 1 ng $^{32}$P-labelled labelled EGS as tag) and increasing amounts of tetra meso (n-methyl 4-pyridyl)porphine (TMP) were set up and added to 200 $\mu$l of bacteria. After 1 hour at room temperature the bacteria were washed three times with 1 ml TB and the radioactivity associated with the bacterial pellet counted.

Figure 1B:
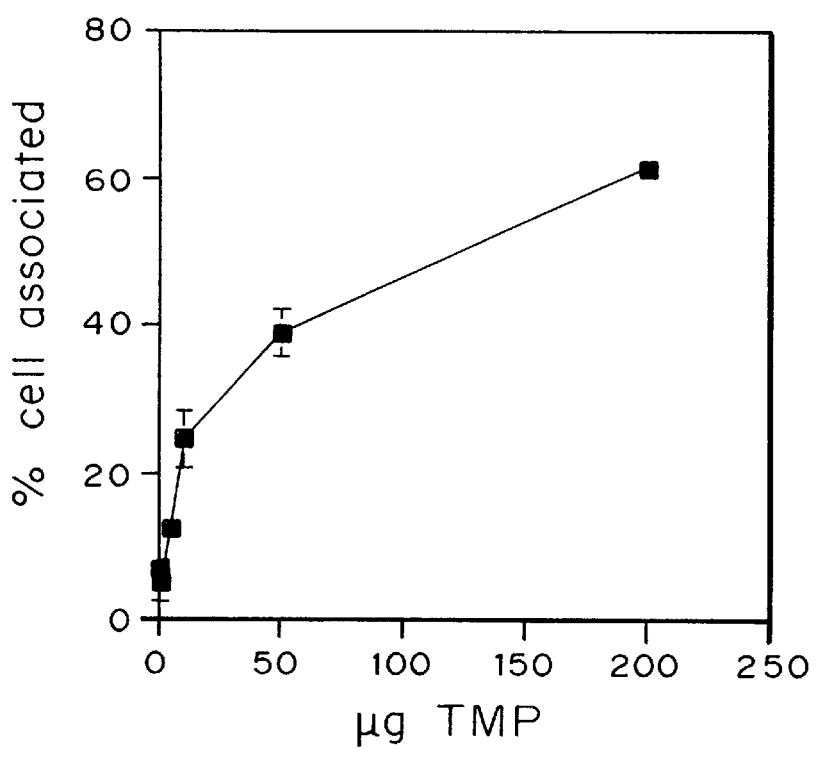
FIG. 1B is a graph of the percentage of cell-associated EGS (percentage of EGS administered) as a function of the number of micrograms of porphyrin originally complexed with the EGS.
Figure 2A:
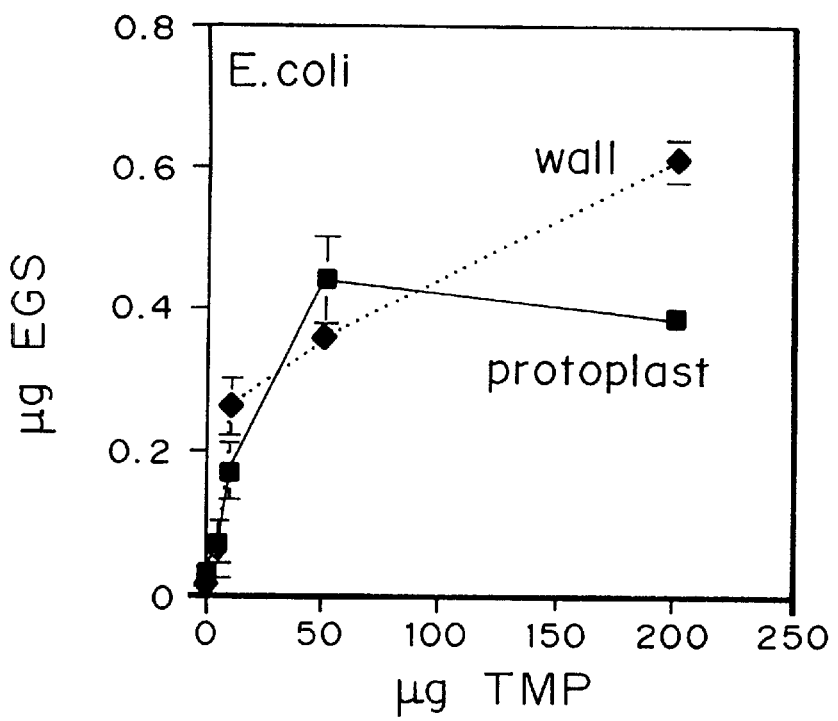
FIGS. 2A, 2B, 2C and 2D are graphs of the number of micrograms of EGS associated with the protoplast (solid lines) or cell wall (dotted lines) of *E. coli, P. aeruginosa, S. aureus,* and *B. subtilis* as a function of the number of micrograms of porphyrin originally complexed with the EGS.
Figure 2B:
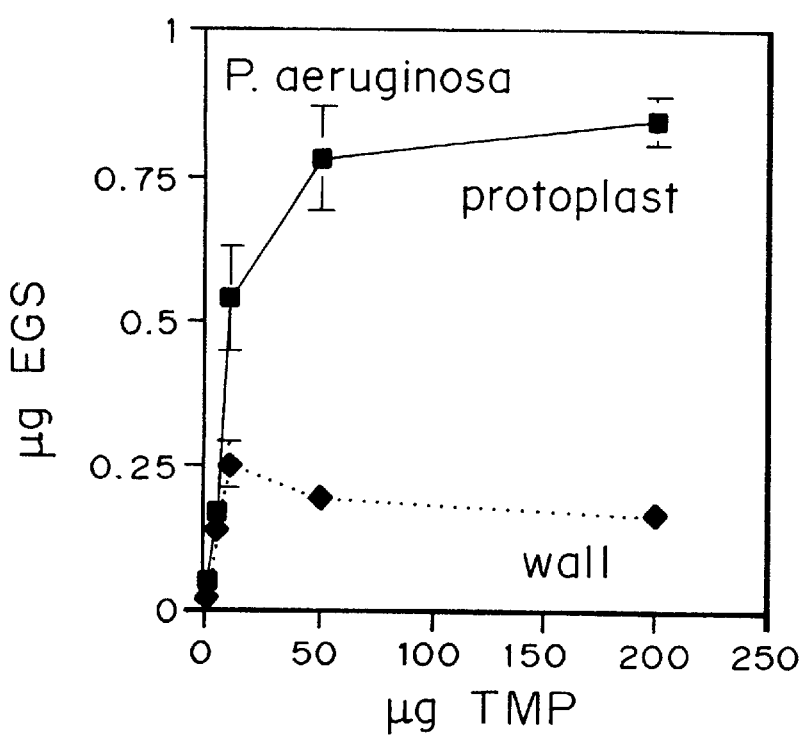
Figure 2C:
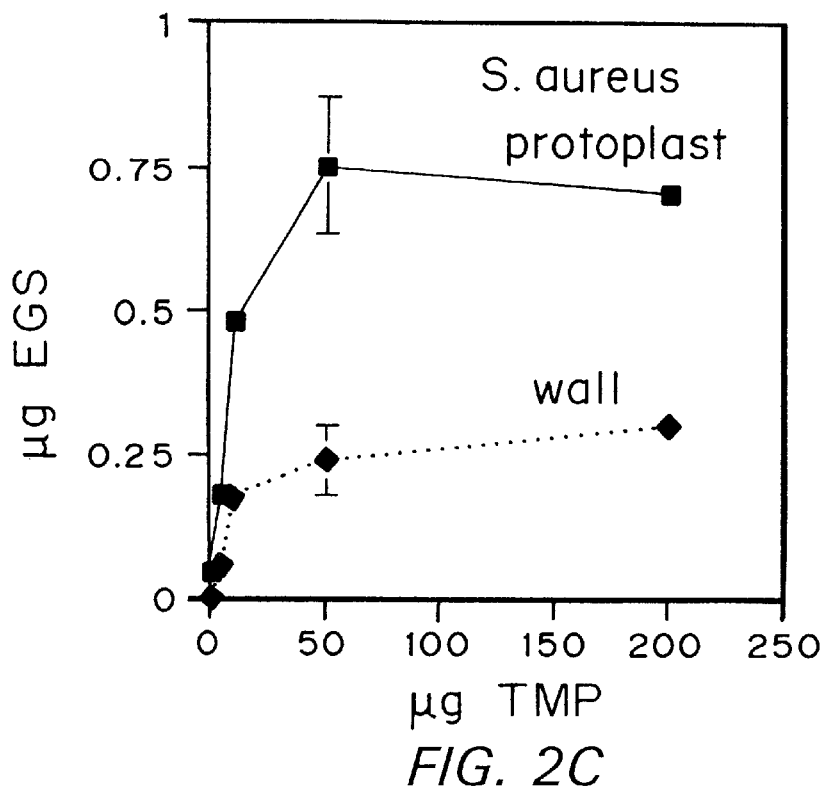
Figure 2D:
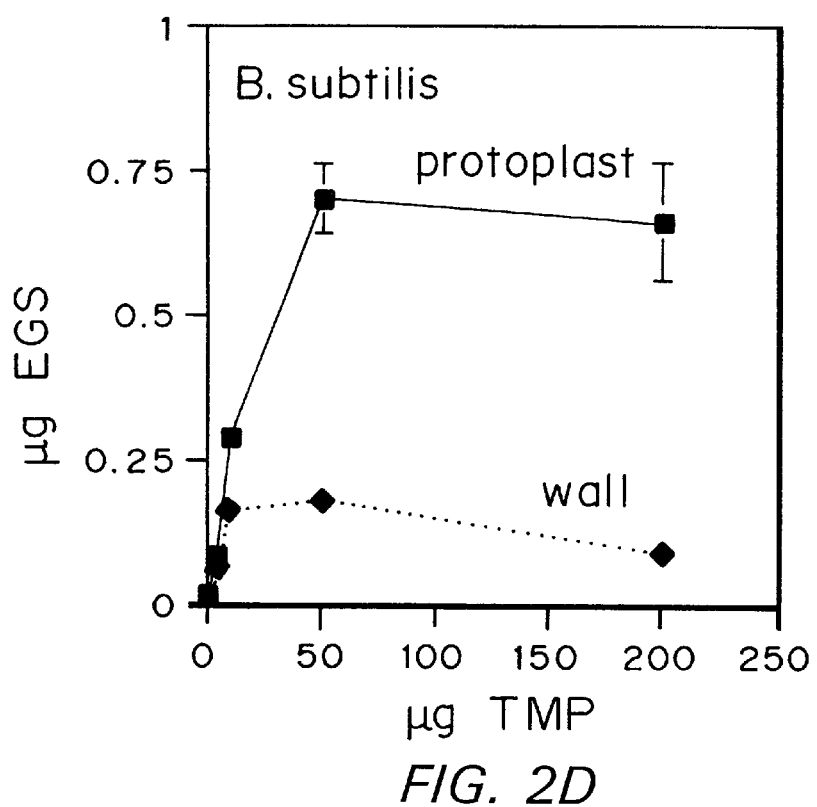

The results are given in FIG. 1. Approximately 6.2% of the delivered EGS was cell-associated in the absence of TMP, whereas up to approximately 60% became cell-associated with 200 $\mu$g TMP (FIG. 1). An OD of 1.0 gives a concentration of approximately $6\times10^8$ cells per ml, therefore approximately 3 $\mu$g EGS became associated with $1.2\times10^8$ bacteria. This computes to $2.2\times10^6$ molecules of EGS per cell. The pellets were then resuspended in gel loading buffer and electrophoresed through a 15% polyacrylamide gel to examine to integrity of the delivered EGS. No significant degradation of the EGS was observed.

The above experiment was repeated at 37° C. and 4° C. to determine if an active uptake process was involved in EGS accumulation in bacteria. There appeared to be no difference in delivery at the various temperatures.

The following experiments were performed to determine that EGS was being incorporated into the cell rather than just being bound to the cell wall. Cells to which the EGS-TMP complex had been delivered were washed extensively with high concentrations of TMP to compete out any EGS-TMP complex that may have been bound to the cells wall. The cells were also treated with high concentrations of RNAase A to degrade any EGS bound to the cell wall, and with lysozyme at the end of the incubation with EGS-TMP to remove cell wall components. After these treatments, the radioactivity associated with the cells was determined. There was no appreciable decrease in cell-associated EGS after all three of the above treatments, thus indicating-that the EGS has been transported to the interior of the bacterium.

This example demonstrates the feasibility of using synthetic oligoribonucleotides for antibacterial therapy. The lack of an effective delivery tool for bacteria has previously hampered such an approach.

Example

Delivery of EGSs to Gram Positive Bacteria

The results in Example 1 indicate enhanced delivery of a nucleic acid to the Gram negative organism *E. coli*. This example demonstrates that porphyrin/nucleic acid complexes allow effective delivery of nucleic acid to gram positive bacteria. *Staphylococcus aureus* (Gram positive), *Pseudomonas aeruginosa* (Gram negative) and *Bacillus subtilis* (Gram positive) were obtained from the ATCC and grown overnight. The bacteria were washed with TB and resuspended to give an OD of 1.0. TMP/EGS complexes were set up as in Example 1 and delivered to the cells.

The cells were washed three times with TB and then treated with lysozyme solutions with EDTA (for Gram negative) or without EDTA (for Gram positive) according to the protocol of Merchant et al., *J. Photochem. Photobiol. B: Biol.* 32:153–157 (1996). The amount of EGS present in the cell pellet and the cell wall fraction was calculated following scintillation counting.

As shown in FIG. 2, TMP was able to deliver EGS to the bacterial species tested, including serious human pathogens known to have the ability to become antibiotic resistant. With excess TMP (50 $\mu$g), up to 75% of the added EGS became distributed into the protoplasts of Pseudomonas, Staphylococcus and Bacillus, while less than 25% of the added EGS remained bound to the cell wall. In *E. coli,* the amount of EGS was approximately the same in the wall and protoplast, with approximately 40% of the added EGS in the protoplast. The relatively high levels of EGS present in the *E. coli* cell wall fraction compared with the other bacterial species may be due to the nature of the *E. coli* cell wall lipopolysaccharide.

From these data it can be calculated that approximately $4.6 \times 10^6$ molecules of EGS are present per bacterial cell—a considerable excess over the number required for RNAase P-mediated inactivation of a target mRNA.

Publications cited herein and the material for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method for converting a drug-resistant eukaryotic cell to a drug-sensitive eukaryotic cell, the method comprising bringing into contact
   (a) the drug-resistant eukaryotic cell, wherein the drug-resistant eukaryotic cell contains a targeted RNA molecule involved in conferring drug resistance to the eukaryotic cell, and
   (b) a RNAase P ribozyme that binds an eukaryotic external guide sequence, or an eukaryotic external guide sequence,
   wherein the RNAase ribozyme or external guide sequence cleaves or promotes RNAase P mediated cleavage of the RNA molecule, respectively, at a specific cleavage site thereby converting the drug-resistant eukaryotic cell to a drug-sensitive eukaryotic cell.

2. The method of claim 1, wherein the eukaryotic cell is an algal cell, a protozoan, a fungal cell, a slime mold cell, or a helminth cell.

3. The method of claim 1 wherein the eukaryotic external guide sequence comprises an RNAase P binding sequence, wherein the RNAase P binding sequence comprises a nucleotide sequence base pairing with itself to form a stem and loop structure similar to the T stem and loop of a precursor tRNA, and
   a recognition sequence complementary to regions of the targeted RNA molecule and comprising an A recognition arm and a D recognition arm, wherein the A recognition arm is located at the 3' end of the RNAase P binding sequence and the D recognition arm is located at the 5' end of the RNAase P binding sequence;
   wherein the stem and loop structure is required for RNAase P catalytic RNA binding to the RNAase P binding sequence and targeted RNA.

4. The method of claim 1, wherein the eukaryotic external guide sequence comprises
   a recognition sequence complementary to a targeted sequence of the target RNA molecule, wherein the recognition sequence comprises an A recognition arm and a T recognition arm, and the targeted sequence comprises, in order from 5' to 3', a first target region, a bulge region, and a second target region,
   wherein the A recognition arm is complementary to the first target region, the T recognition arm is complementary to the second target region, and the T recognition arm is located 5' of and adjacent to the A recognition arm.

5. The method of claim 1, wherein the step of bringing into contact is accomplished by administering the RNAase P ribozyme or external guide sequence to an animal or plant infected by the drug-resistant cell or an organism comprising the drug-resistant eukaryotic cell.

6. The method of claim 1, wherein the step of bringing into contact is accomplished by bringing into contact the drug resistant cell and a nucleic acid encoding the RNAase P ribozyme or external guide sequence.

7. The method of claim 6 wherein the step of bringing into contact is accomplished by administering nucleic acid encoding the RNAase P ribozyme or external guide sequence to an animal or plant infected by the drug-resistant cell or an organism comprising the drug-resistant eukaryotic cell.

8. The method of claim 1, further comprising bringing into contact the drug-sensitive eukaryotic cell and a drug to which the drug-sensitive eukaryotic cell is sensitive.

* * * * *

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 50 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: no (xi) SEQUENCE DESCRIPTION: SEQ ID NO: 1:

CUGGAUGUGU CUGCGGCGUU UUAUCAUCUU CCUCUUCAUC CUGCUGCUAU      50

(2) INFORMATION FOR SEQ ID NO: 2:

(i) SEQUENCE CHARACTERISTICS:
      (A) LENGTH: 13 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: no (xi) SEQUENCE DESCRIPTION: SEQ ID NO: 2:

GAGGAAACGC CGC      13

(2) INFORMATION FOR SEQ ID NO: 3:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: no (xi) SEQUENCE DESCRIPTION: SEQ ID NO: 3:

GAUAAAGAAG GUUCGAAUCC UUCACGCCGC      30